(12) United States Patent
Wightman et al.

(10) Patent No.: US 8,333,525 B2
(45) Date of Patent: Dec. 18, 2012

(54) CLICK PEN APPLICATOR DEVICE AND METHOD OF USING SAME

(75) Inventors: James C. Wightman, Livingston, NJ (US); Michael Furey, Holtsville, NY (US); Jeff Hayet, Wayne, NJ (US); Robert C. Johnson, Memphis, TN (US)

(73) Assignee: MSD Consumer Care, Inc., Memphis, TN (US)

( * ) Notice: Subject to any disclaimer, the term of this patent is extended or adjusted under 35 U.S.C. 154(b) by 0 days.

(21) Appl. No.: 13/563,269

(22) Filed: Jul. 31, 2012

(65) Prior Publication Data

US 2012/0291910 A1 Nov. 22, 2012

Related U.S. Application Data

(62) Division of application No. 13/301,379, filed on Nov. 21, 2011.

(60) Provisional application No. 61/415,522, filed on Nov. 19, 2010.

(51) Int. Cl.
*B43K 5/06* (2006.01)
(52) U.S. Cl. ......... 401/174; 401/171; 401/265; 222/390
(58) Field of Classification Search .................... 401/17, 401/174, 261–263, 265, 266, 277, 68, 70, 401/75; 222/386, 390
See application file for complete search history.

(56) References Cited

U.S. PATENT DOCUMENTS

| | | | |
|---|---|---|---|
| 2,547,287 A | 4/1951 | Sanders et al. | |
| 3,351,074 A | 11/1967 | Aston | |
| 3,756,729 A | 9/1973 | Tufts | |
| 3,756,732 A | 9/1973 | Stoffler | |
| 4,002,182 A | 1/1977 | Michel | |
| 4,548,524 A | 10/1985 | Seager | |
| 4,750,502 A | 6/1988 | Ser et al. | |
| 4,838,722 A | 6/1989 | Katz | |
| 4,865,591 A | 9/1989 | Sams | |
| 4,892,427 A | 1/1990 | Ford | |
| 4,911,570 A | 3/1990 | Rhoades | |
| 5,011,317 A | 4/1991 | Gueret | |
| 5,131,774 A | 7/1992 | Katz | |
| 5,207,659 A | 5/1993 | Pennaneac'h et al. | |
| 5,339,841 A | 8/1994 | Gueret | |
| 5,613,957 A | 3/1997 | Py | |
| 5,738,067 A | 4/1998 | Landwehr et al. | |
| 5,772,347 A | 6/1998 | Gueret | |
| 5,871,020 A | 2/1999 | DeVone | |
| 5,879,095 A | 3/1999 | Gueret | |
| 6,053,184 A | 4/2000 | DeVone | |

(Continued)

FOREIGN PATENT DOCUMENTS

DE 3538653 5/1987

(Continued)

OTHER PUBLICATIONS

"Medical Wart & Corn Pen," Medical Brands, http://medicalbrands.eu/files/downloads/Wart_Removal_Pen.pdf.

(Continued)

*Primary Examiner* — David Walczak
(74) *Attorney, Agent, or Firm* — Kenyon & Kenyon LLP

(57) ABSTRACT

A click pen applicator device that provides predetermined dosing of the formulation for precise application, and rapidly primes the formulation using the dosing click mechanism to prepare the applicator for use.

9 Claims, 28 Drawing Sheets

U.S. PATENT DOCUMENTS

| | | | |
|---|---|---|---|
| 6,053,893 | A | 4/2000 | Bucher |
| 6,186,686 | B1 | 2/2001 | Neuner et al. |
| 6,193,698 | B1 | 2/2001 | Kirchhofer et al. |
| 6,200,055 | B1 | 3/2001 | Fusaro, Jr. |
| 6,221,053 | B1 * | 4/2001 | Walters et al. ............... 604/211 |
| 6,435,751 | B1 | 8/2002 | Ono et al. |
| 6,551,000 | B2 | 4/2003 | Kandasamy et al. |
| 6,688,317 | B2 | 2/2004 | Gueret |
| 6,729,787 | B2 | 5/2004 | Usami et al. |
| 6,745,781 | B2 | 6/2004 | Gueret |
| 7,086,796 | B2 | 8/2006 | Severa |
| 7,201,527 | B2 | 4/2007 | Thorpe et al. |
| 7,226,231 | B2 | 6/2007 | Py et al. |
| 7,252,449 | B2 | 8/2007 | Carroll |
| 7,309,185 | B2 | 12/2007 | Thorpe et al. |
| 7,316,670 | B2 * | 1/2008 | Graf et al. ............... 604/207 |
| 7,427,275 | B2 * | 9/2008 | DeRuntz et al. ............... 604/207 |
| 7,476,048 | B2 | 1/2009 | Prague |
| 7,500,966 | B2 | 3/2009 | Hommann |
| 7,563,048 | B2 | 7/2009 | Koptis |
| 7,607,852 | B2 | 10/2009 | Washington |
| 7,608,642 | B2 | 10/2009 | Malik |
| 7,651,291 | B2 | 1/2010 | Py et al. |
| 7,665,923 | B2 | 2/2010 | Py et al. |
| 7,794,166 | B2 | 9/2010 | Zhang |
| 2005/0063766 | A1 | 3/2005 | Chen et al. |
| 2006/0072963 | A1 | 4/2006 | Thorpe et al. |
| 2006/0206057 | A1 | 9/2006 | DeRuntz et al. |
| 2006/0207627 | A1 | 9/2006 | Thorpe et al. |
| 2006/0210351 | A1 | 9/2006 | Losier et al. |
| 2007/0020038 | A1 | 1/2007 | Tani |
| 2008/0101850 | A1 | 5/2008 | Wojcik et al. |
| 2008/0298876 | A1 | 12/2008 | Porter et al. |
| 2008/0314405 | A1 | 12/2008 | Chu et al. |
| 2009/0097899 | A1 | 4/2009 | Carroll |
| 2009/0311036 | A1 | 12/2009 | Pires et al. |
| 2010/0284725 | A1 | 11/2010 | Zhang |
| 2011/0052309 | A1 | 3/2011 | Wu |
| 2011/0076089 | A1 | 3/2011 | Geminiani |
| 2011/0116857 | A1 | 5/2011 | Carroll et al. |
| 2011/0129288 | A1 | 6/2011 | Uehara |
| 2011/0182649 | A1 | 7/2011 | Rolion et al. |
| 2011/0200383 | A1 | 8/2011 | Gieux |
| 2011/0240589 | A1 | 10/2011 | Averill |
| 2011/0250007 | A1 | 10/2011 | Kang |

FOREIGN PATENT DOCUMENTS

| | | |
|---|---|---|
| EP | 730876 | 9/1996 |
| EP | 1074273 | 2/2001 |
| EP | 1304129 | 4/2003 |
| EP | 1545663 | 6/2005 |
| EP | 1587562 | 10/2005 |
| JP | 09001981 | 1/1997 |
| JP | 2001087386 | 4/2001 |

OTHER PUBLICATIONS

"Drug Enhancement Company of America Licenses Oculus—Microcyn (R) Technology for Use in First Responder 'Pen-Like' Applicator," PR Newswire, Jun. 14, 2007.

International Search Report, dated Mar. 30, 2012, from corresponding International Patent Application No. PCT/US2011/061327 filed Nov. 18, 2011.

* cited by examiner

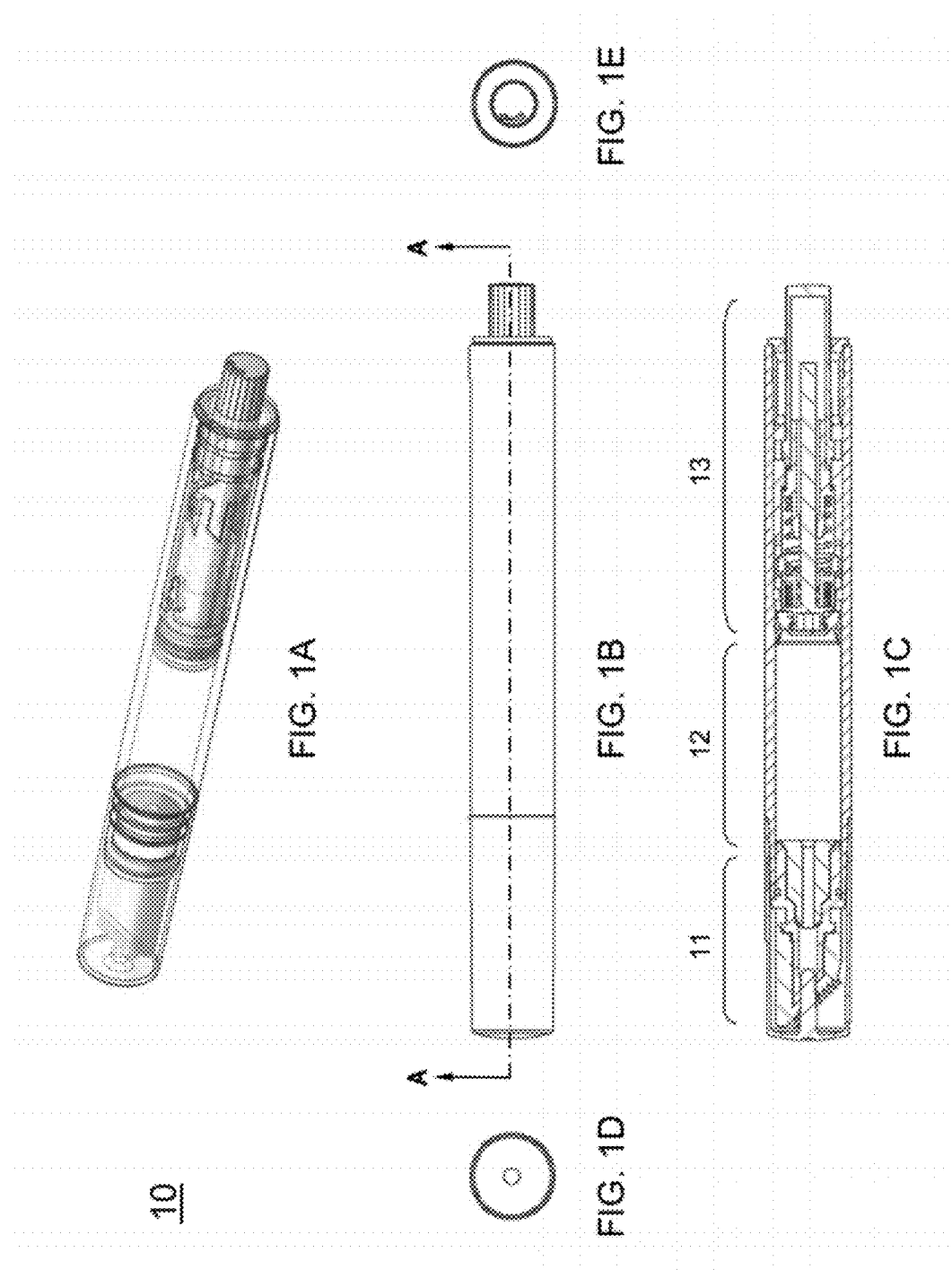

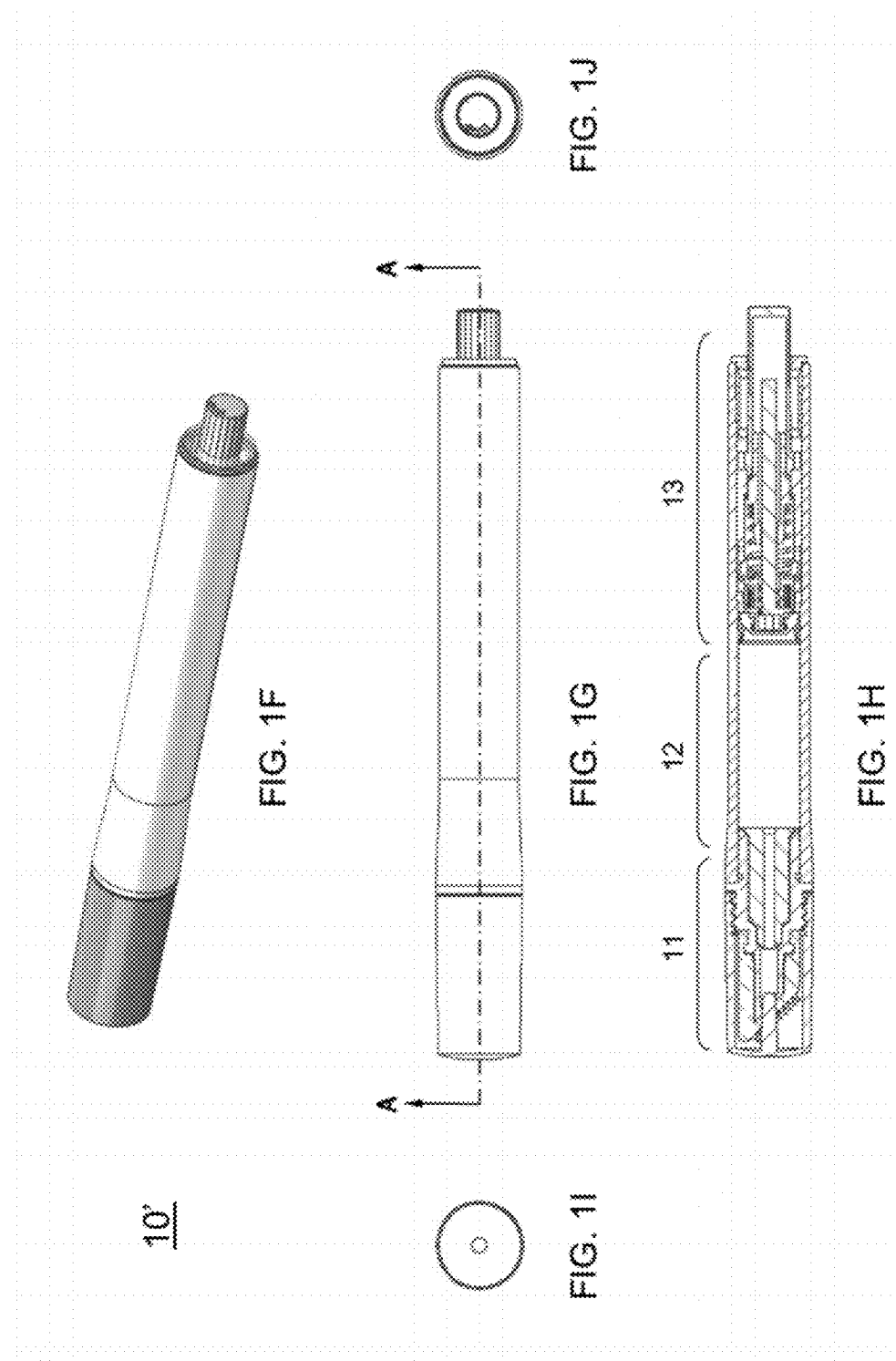

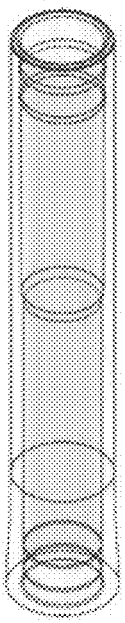
FIG. 2F
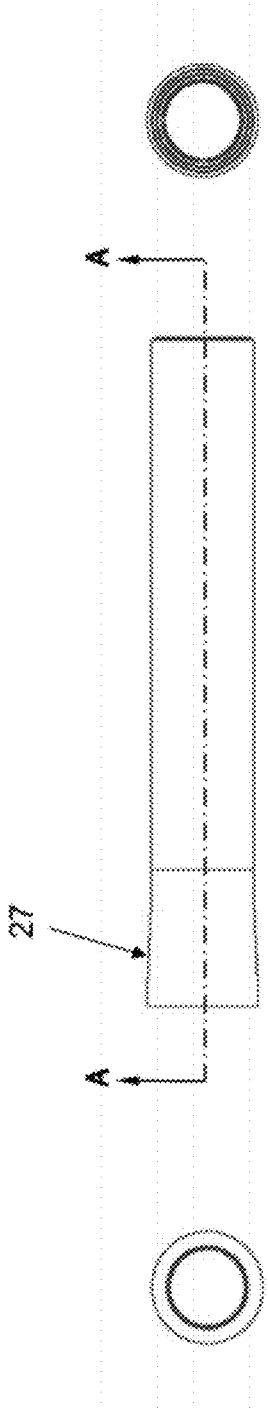
FIG. 2G
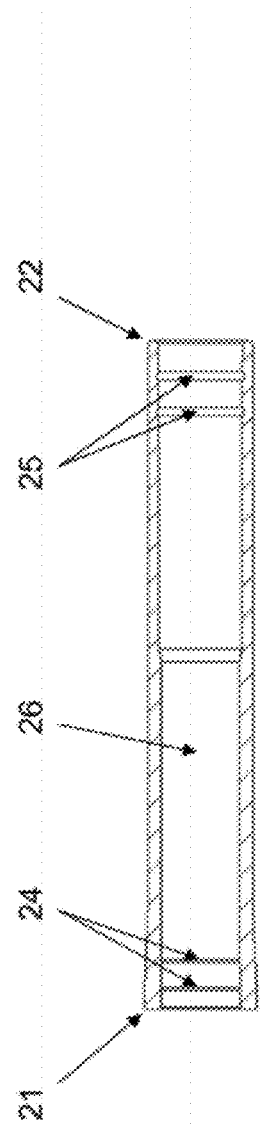
FIG. 2H
FIG. 2J
FIG. 2I

40

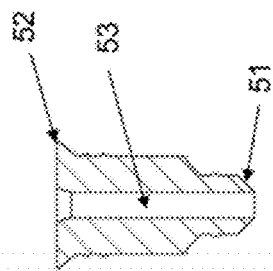
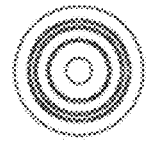
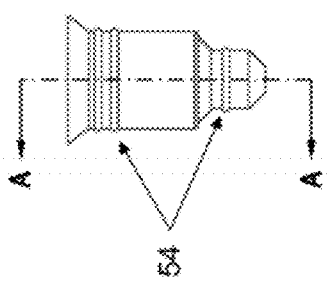
FIG. 5C
FIG. 5D
FIG. 5B
FIG. 5E
FIG. 5A

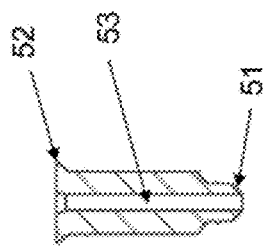
FIG. 5H
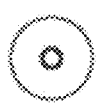
FIG. 5I
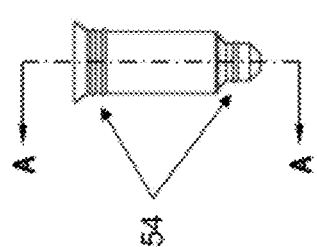
FIG. 5G
FIG. 5J
FIG. 5F

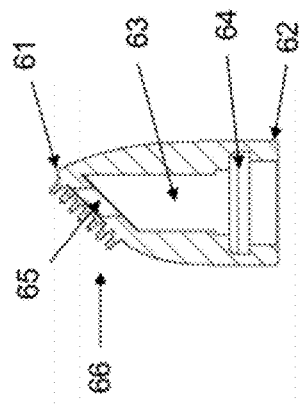
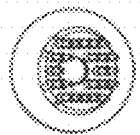
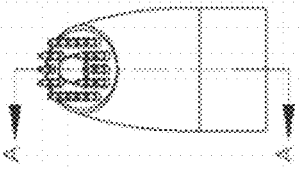
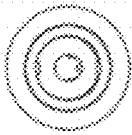

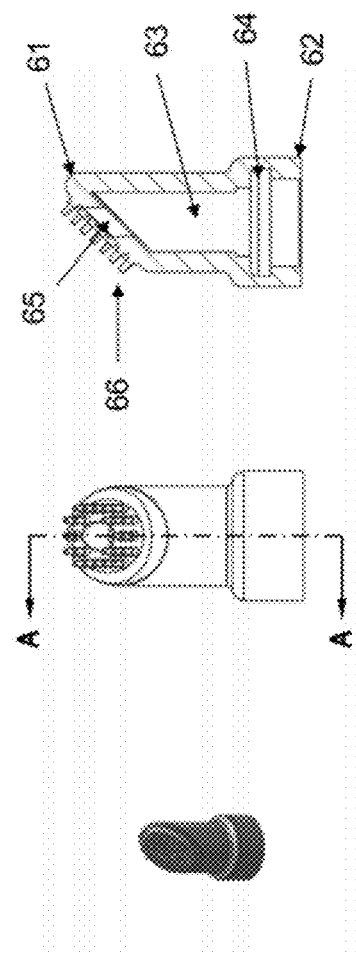

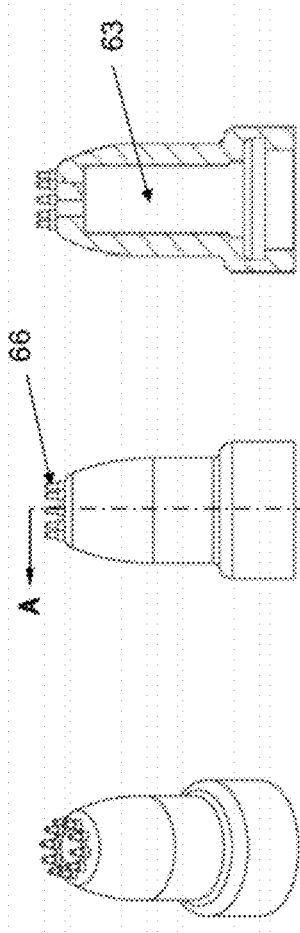
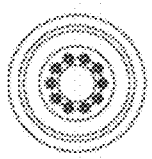
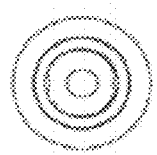
FIG. 6U  FIG. 6V  FIG. 6W  FIG. 6X  FIG. 6Y

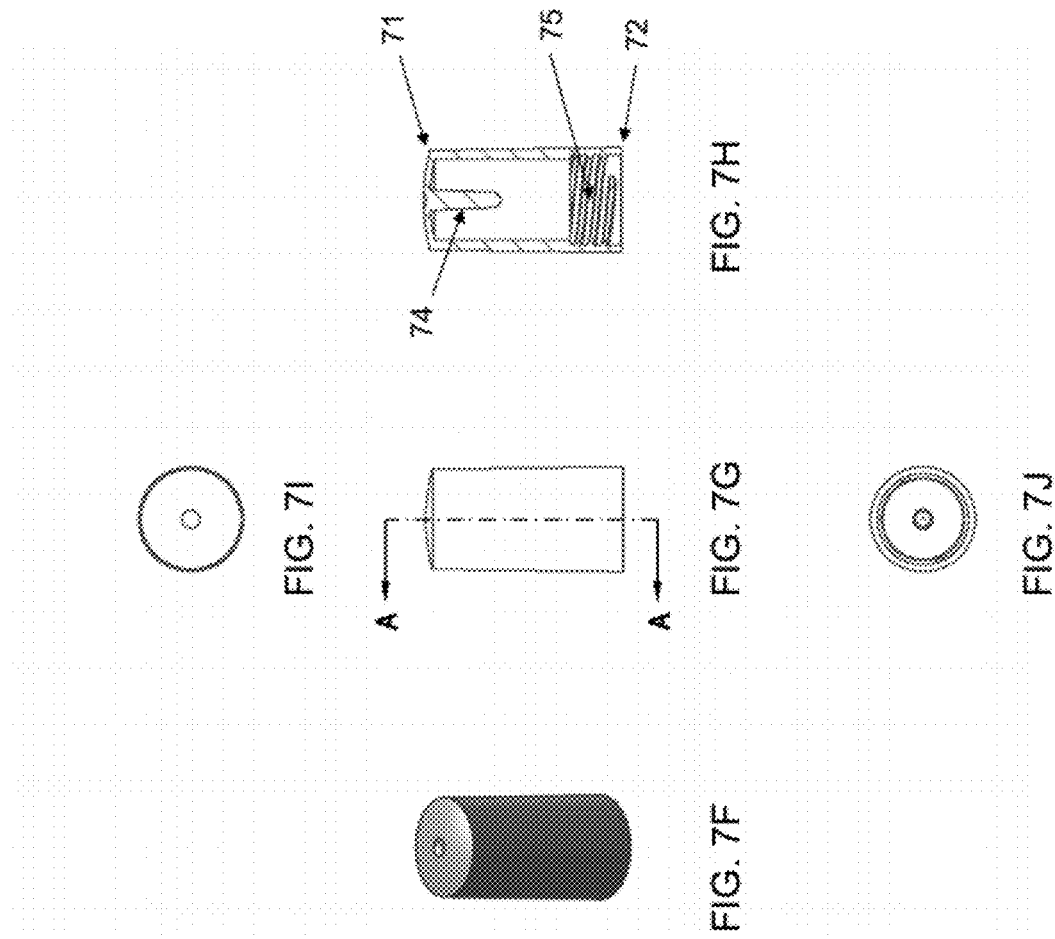

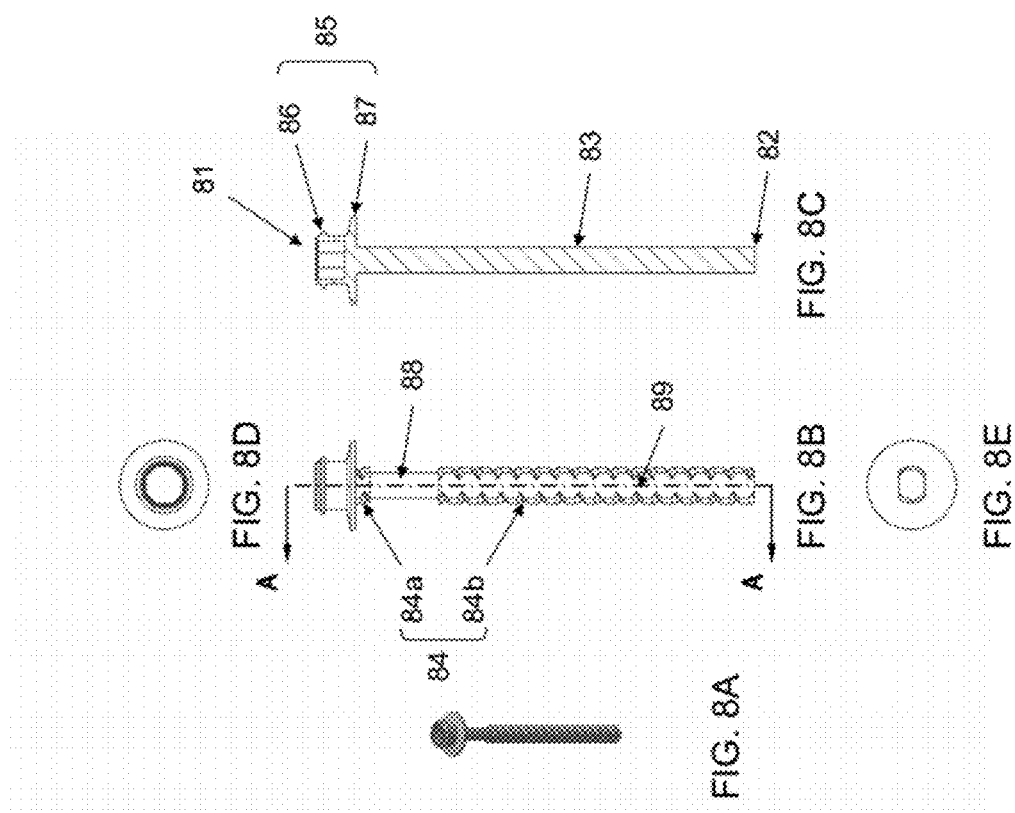

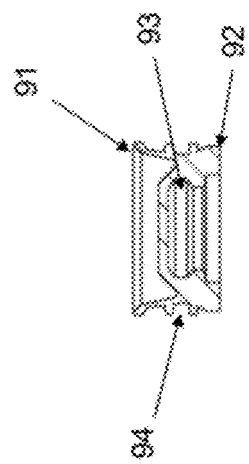
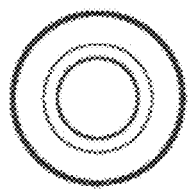
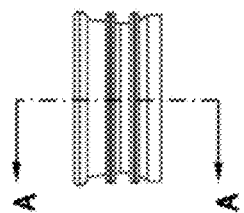
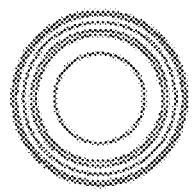

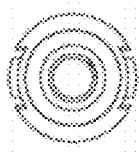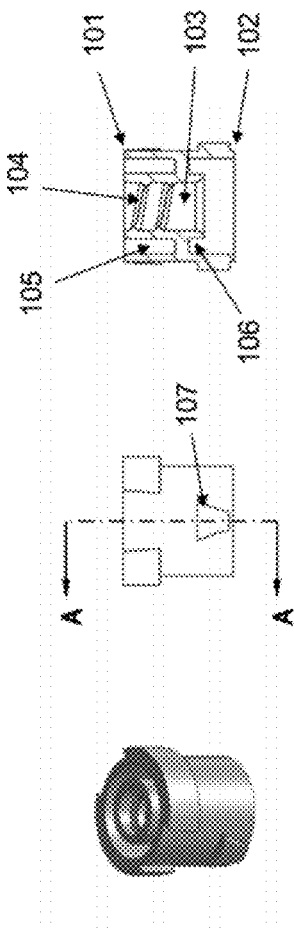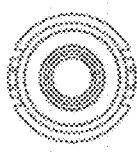

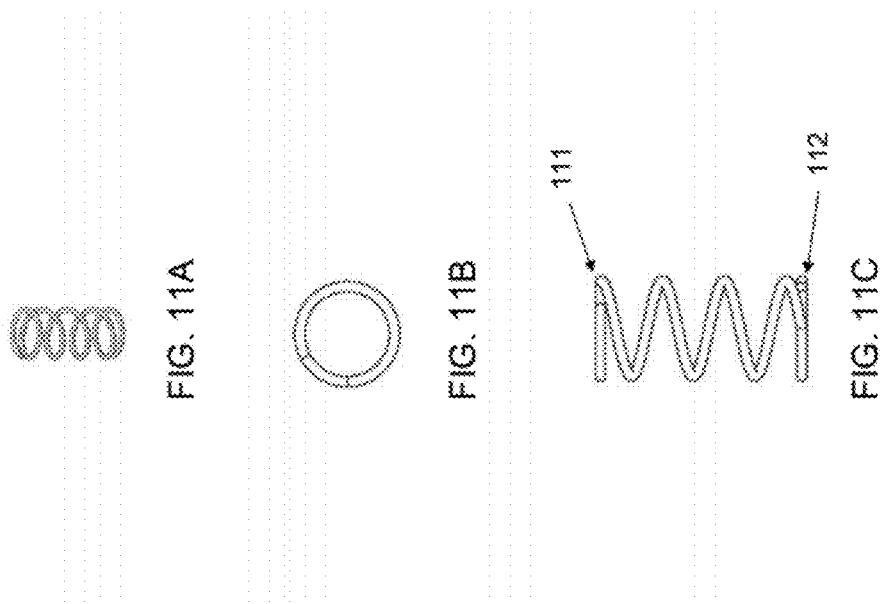

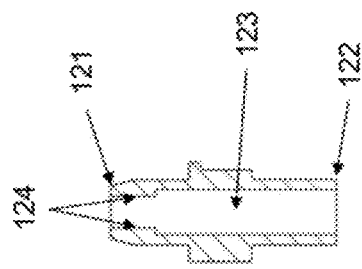
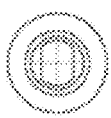
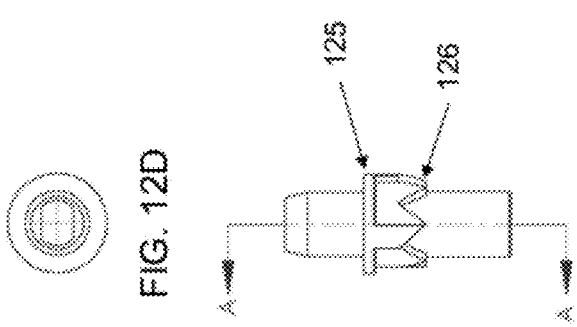
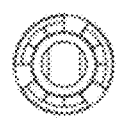
FIG. 12C
FIG. 12D   FIG. 12B   FIG. 12E
FIG. 12A

130

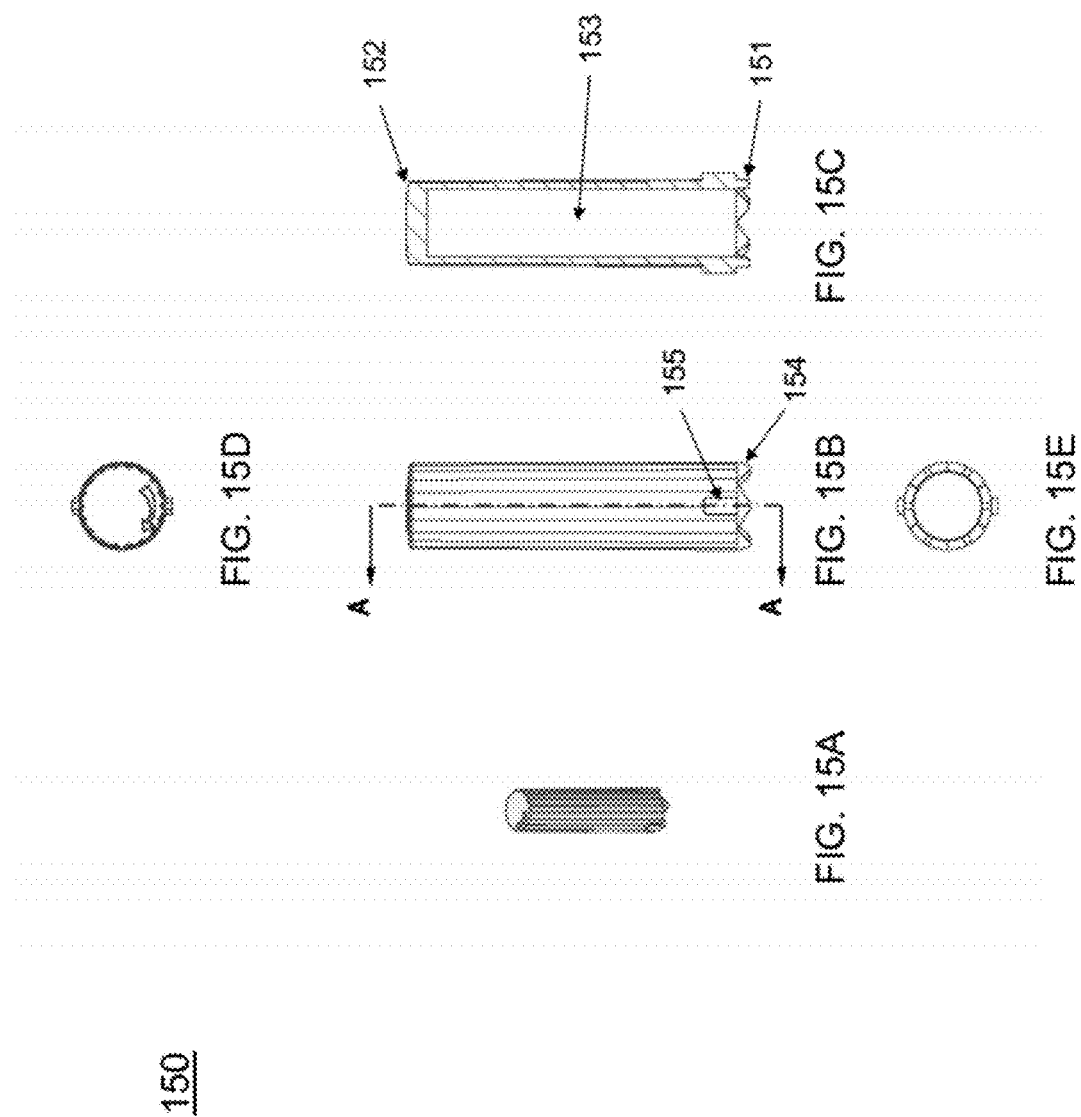

CLICK PEN APPLICATOR DEVICE AND METHOD OF USING SAME

CROSS-REFERENCE TO RELATED APPLICATION

The present application is a divisional application of U.S. patent application Ser. No. 13/301,379, filed on Nov. 21, 2011, and is based upon and claims the benefit of priority from the prior U.S. Provisional Application Ser. No. 61/415,522, filed on Nov. 19, 2010, the entire contents of which are incorporated herein by reference.

FIELD OF THE INVENTION

The present invention relates to a click pen applicator device, and a method of using the click pen applicator device.

BACKGROUND

Existing pen applicators generally utilize a twist function for dispensing a formulation from the pen applicator. These twist pen applicators generally include a rotating portion that is twisted or rotated relative to the remaining portion of the applicator, thereby advancing a formulation contained within the twist pen applicator. However, such twist pen applicators do not provide a predetermined dose of the formulation since the rotating portion is generally freely rotatable. Accordingly, a user is required to make a determination as to the appropriate amount of the formulation to dispense for a particular application. In addition, twist pen applicators may suffer from sealing problems. Further, such twist pen applicators generally require a substantial number of rotations of the rotating portion before the twist pen applicator is primed and ready to dispense the formulation.

Click pen applicators generally include an actuating portion that is pressed, or clicked, relative to the remaining portion of the applicator, thereby advancing a formulation contained within the click pen applicator. Further, such click pen applicators are conventionally known to have sealing problems that may render them less desirable than twist pen applicators, especially for formulations that may require better sealing, such as those that may tend to evaporate or experience weight loss over time. Further, click pen applicators also generally require a substantial number of clicks of the actuating portion before the click pen applicator is primed and ready to dispense the formulation. A prior art click pen 170 is illustrated in FIGS. 17 and 18.

Thus, existing pen applicators share the common problems of inadequate sealing, uncontrolled delivery of the formulation, and excessive number of actuations before the applicator is primed and ready for use. For example, inadequate sealing may result in the formulation's evaporating while the applicator is merely in storage between uses. In addition, uncontrolled delivery may result in a user's applying too much or too little of the formulation for the particular application, potentially having harmful or ineffective results. Further, excessive number of actuations for priming may lead to a user's believing that the applicator is broken, non-functional, empty, dried up, or otherwise unusable, when the applicator is in fact functional but not yet fully primed for use.

SUMMARY

Accordingly, there is a need for an applicator that improves sealing of the formulation to reduce evaporation and/or weight loss, provides predetermined dosing of the formulation for precise application, and rapidly primes the formulation to prepare the applicator for immediate use.

In a non-limiting embodiment of the present invention, a device for dispensing a formulation comprises a centerband having a proximal end and a distal end and defining a storage section having the formulation disposed within; an applicator section situated at the distal end of the centerband; and a multistage actuator section situated at the proximal end of the centerband for rapid priming with a click dispensing mechanism with a piston seat having two sets of external threads on a shaft with an unthreaded length therebetween.

In an alternative non-limiting embodiment of the invention, the multistage actuator section comprises a spiral having internal threads configured to engage with the external threads of the piston seat; and a priming spring operatively engaged between the piston seat and the spiral.

In an alternative non-limiting embodiment of the invention, the two sets of external threads of the piston seat have a same pitch.

In an alternative non-limiting embodiment of the invention, a first set of the two sets of external threads includes a length shorter than that of a second set of the two sets of external threads.

In an alternative non-limiting embodiment of the invention, a pitch of a second set of the two sets of external threads is configured to dispense a discrete dose with each dispensing actuation.

In an alternative non-limiting embodiment of the invention, the priming spring is configured to expand over the unthreaded length of the piston seat when the internal threads of the spiral do not engage the external threads of the piston seat.

In an alternative non-limiting embodiment of the invention, the multistage actuator section further comprises a cup attached to a distal end of the piston seat; a seal between the cup and the proximal end of the centerband; a gear operatively engaged with the shaft of the piston seat; a click spring operatively disposed between the gear and the spiral; and a spiral sleeve and a push button operatively engaged with the gear, the push button having a locking element.

In an alternative non-limiting embodiment of the invention, the applicator section comprises a passing seat attached to the distal end of the centerband; a seal between the passing seat and the distal end of the centerband; an orifice reducer situated inside the passing seat; a nose attached to a distal end of the passing seat; and a cap attached to the distal end of the centerband.

In an alternative non-limiting embodiment of the invention, the cap includes a pintel configured to seal at least one of the nose and the passing seat of the applicator section.

In an alternative non-limiting embodiment of the invention, the seal between the cup and the proximal end of the centerband is an o-ring, and the seal between the passing seat and the distal end of the centerband is an o-ring.

In an alternative non-limiting embodiment of the invention, the formulation comprises salicylic acid.

In yet another non-limiting embodiment of the present invention, a method of priming and dosing a formulation using a click pen dispensing device comprises priming the formulation at a priming rate using a click actuator with a piston seat having two sets of external threads on a shaft with an unthreaded length therebetween; and dosing the formulation at a dosing rate different from the priming rate using the click actuator.

In an alternative non-limiting embodiment of the present invention, the click actuator is actuated using one hand.

In an alternative non-limiting embodiment of the invention, the click actuator includes a locking element for preventing the priming and the dosing.

In an alternative non-limiting embodiment of the invention, the formulation comprises salicylic acid.

In an alternative non-limiting embodiment of the invention, the priming step includes at least one fine priming rate and a gross priming rate.

In an alternative non-limiting embodiment of the invention, the dosing step dispenses a predetermined dose of the formulation, and the priming step dispenses a predetermined priming dose of the formulation.

In yet another non-limiting embodiment of the present invention, a method of dispensing a formulation, using a device comprising a centerband having a proximal end and a distal end and defining a storage section having a distal end and a proximal end and having the formulation disposed within, an applicator section situated at the distal end of the centerband, and a multistage actuator section situated at the proximal end of the centerband, comprises priming the device by priming actuations of the multistage actuator section with a piston seat having two sets of external threads on a shaft with an unthreaded length therebetween, the priming step comprising a gross priming actuation displacing a volume greater than that of a predetermined dose; dispensing the predetermined dose of the formulation, via the applicator section, by subsequent dispensing actuations of the multistage actuator section; and applying the predetermined dose via the applicator section.

In an alternative non-limiting embodiment of the invention, the priming step comprises at least one fine priming actuation displacing a volume less than that of the gross priming actuation.

In an alternative non-limiting embodiment of the invention, the priming step comprises at least one fine priming actuation displacing a volume equal to that of the predetermined dose.

Other features and aspects of the present invention will become more fully apparent from the following brief description of the drawings, the detailed description of the non-limiting embodiments, the appended claims and the accompanying drawings.

BRIEF DESCRIPTION OF THE DRAWINGS

FIG. 1A illustrates a schematic perspective view of an exemplary embodiment of an assembled click pen applicator device according to the present invention.

FIG. 1B illustrates a schematic side view of the exemplary embodiment of FIG. 1A.

FIG. 1C illustrates a schematic cross-sectional view taken along line A-A shown in FIG. 1B of the exemplary embodiment of FIG. 1B.

FIG. 1D illustrates a schematic top view of the exemplary embodiment of FIG. 1A.

FIG. 1E illustrates a schematic bottom view of the exemplary embodiment of FIG. 1A.

FIG. 1F illustrates a schematic perspective view of another exemplary embodiment of an assembled click pen applicator device according to the present invention.

FIG. 1G illustrates a schematic side view of the exemplary embodiment of FIG. 1F.

FIG. 1H illustrates a schematic cross-sectional view taken along line A-A shown in FIG. 1G of the exemplary embodiment of FIG. 1G.

FIG. 1I illustrates a schematic top view of the exemplary embodiment of FIG. 1F.

FIG. 1J illustrates a schematic bottom view of the exemplary embodiment of FIG. 1F.

FIG. 2F illustrates a schematic perspective view of another exemplary embodiment of a centerband according to the present invention.

FIG. 2G illustrates a schematic side view of the exemplary embodiment of FIG. 2F.

FIG. 2H illustrates a schematic cross-sectional view taken along line A-A shown in FIG. 2G of the exemplary embodiment of FIG. 2G.

FIG. 2I illustrates a schematic top view of the exemplary embodiment of FIG. 2F.

FIG. 2J illustrates a schematic bottom view of the exemplary embodiment of FIG. 2F.

FIG. 5A illustrates a schematic perspective view of an exemplary embodiment of an orifice reducer according to the present invention.

FIG. 5B illustrates a schematic side view of the exemplary embodiment of FIG. 5A.

FIG. 5C illustrates a schematic cross-sectional view taken along line A-A shown in FIG. 5B of the exemplary embodiment of FIG. 5B.

FIG. 5D illustrates a schematic top view of the exemplary embodiment of FIG. 5A.

FIG. 5E illustrates a schematic bottom view of the exemplary embodiment of FIG. 5A.

FIG. 5F illustrates a schematic perspective view of another exemplary embodiment of an orifice reducer according to the present invention.

FIG. 5G illustrates a schematic side view of the exemplary embodiment of FIG. 5F.

FIG. 5H illustrates a schematic cross-sectional view taken along line A-A shown in FIG. 5G of the exemplary embodiment of FIG. 5G.

FIG. 5I illustrates a schematic top view of the exemplary embodiment of FIG. 5F.

FIG. 5J illustrates a schematic bottom view of the exemplary embodiment of FIG. 5F.

FIG. 6A illustrates a schematic perspective view of an exemplary embodiment of a nose according to the present invention.

FIG. 6B illustrates a schematic side view of the exemplary embodiment of FIG. 6A.

FIG. 6C illustrates a schematic cross-sectional view taken along line A-A shown in FIG. 6B of the exemplary embodiment of FIG. 6B.

FIG. 6D illustrates a schematic top view of the exemplary embodiment of FIG. 6A.

FIG. 6E illustrates a schematic bottom view of the exemplary embodiment of FIG. 6A.

FIG. 6F illustrates a schematic perspective view of another exemplary embodiment of a nose according to the present invention.

FIG. 6G illustrates a schematic side view of the exemplary embodiment of FIG. 6F.

FIG. 6H illustrates a schematic cross-sectional view taken along line A-A shown in FIG. 6G of the exemplary embodiment of FIG. 6G.

FIG. 6I illustrates a schematic top view of the exemplary embodiment of FIG. 6F.

FIG. 6J illustrates a schematic bottom view of the exemplary embodiment of FIG. 6F.

FIG. 6U illustrates a schematic perspective view of yet another exemplary embodiment of a nose according to the present invention.

FIG. 6V illustrates a schematic side view of the exemplary embodiment of FIG. 6U.

FIG. 6W illustrates a schematic cross-sectional view taken along line A-A shown in FIG. 6V of the exemplary embodiment of FIG. 6V.

FIG. 6X illustrates a schematic top view of the exemplary embodiment of FIG. 6U.

FIG. 6Y illustrates a schematic bottom view of the exemplary embodiment of FIG. 6U.

FIG. 7F illustrates a schematic perspective view of another exemplary embodiment of a cap according to the present invention.

FIG. 7G illustrates a schematic side view of the exemplary embodiment of FIG. 7F.

FIG. 7H illustrates a schematic cross-sectional view taken along line A-A shown in FIG. 7G of the exemplary embodiment of FIG. 7G.

FIG. 7I illustrates a schematic top view of the exemplary embodiment of FIG. 7F.

FIG. 7J illustrates a schematic bottom view of the exemplary embodiment of FIG. 7F.

FIG. 8A illustrates a schematic perspective view of an exemplary embodiment of a piston seat according to the present invention.

FIG. 8B illustrates a schematic side view of the exemplary embodiment of FIG. 8A.

FIG. 8C illustrates a schematic cross-sectional view taken along line A-A shown in FIG. 8B of the exemplary embodiment of FIG. 8B.

FIG. 8D illustrates a schematic top view of the exemplary embodiment of FIG. 8A.

FIG. 8E illustrates a schematic bottom view of the exemplary embodiment of FIG. 8A.

FIG. 9A illustrates a schematic perspective view of an exemplary embodiment of a cup according to the present invention.

FIG. 9B illustrates a schematic side view of the exemplary embodiment of FIG. 9A.

FIG. 9C illustrates a schematic cross-sectional view taken along line A-A shown in FIG. 9B of the exemplary embodiment of FIG. 9B.

FIG. 9D illustrates a schematic top view of the exemplary embodiment of FIG. 9A.

FIG. 9E illustrates a schematic bottom view of the exemplary embodiment of FIG. 9A.

FIG. 10A illustrates a schematic perspective view of an exemplary embodiment of a spiral according to the present invention.

FIG. 10B illustrates a schematic side view of the exemplary embodiment of FIG. 10A.

FIG. 10C illustrates a schematic cross-sectional view taken along line A-A shown in FIG. 10B of the exemplary embodiment of FIG. 10B.

FIG. 10D illustrates a schematic top view of the exemplary embodiment of FIG. 10A.

FIG. 10E illustrates a schematic bottom view of the exemplary embodiment of FIG. 10A.

FIG. 11A illustrates a schematic perspective view of an exemplary embodiment of a priming spring according to the present invention.

FIG. 11B illustrates a schematic top view of the exemplary embodiment of FIG. 11A.

FIG. 11C illustrates a schematic side view of the exemplary embodiment of FIG. 11A.

FIG. 12A illustrates a schematic perspective view of an exemplary embodiment of a gear according to the present invention.

FIG. 12B illustrates a schematic side view of the exemplary embodiment of FIG. 12A.

FIG. 12C illustrates a schematic cross-sectional view taken along line A-A shown in FIG. 12B of the exemplary embodiment of FIG. 12B.

FIG. 12D illustrates a schematic top view of the exemplary embodiment of FIG. 12A.

FIG. 12E illustrates a schematic bottom view of the exemplary embodiment of FIG. 12A.

FIG. 15A illustrates a schematic perspective view of an exemplary embodiment of a push button according to the present invention.

FIG. 15B illustrates a schematic side view of the exemplary embodiment of FIG. 15A.

FIG. 15C illustrates a schematic cross-sectional view taken along line A-A shown in FIG. 15B of the exemplary embodiment of FIG. 15B.

FIG. 15D illustrates a schematic top view of the exemplary embodiment of FIG. 15A.

FIG. 15E illustrates a schematic bottom view of the exemplary embodiment of FIG. 15A.

FIG. 17D illustrates a schematic top view of the prior art click pen applicator device of FIG. 17A.

FIG. 17E illustrates a schematic bottom view of the prior art click pen applicator device of FIG. 17A.

FIG. 18 illustrates a schematic perspective, exploded view of a prior art click pen applicator device.

DETAILED DESCRIPTION OF THE EMBODIMENTS

Figure 2A:
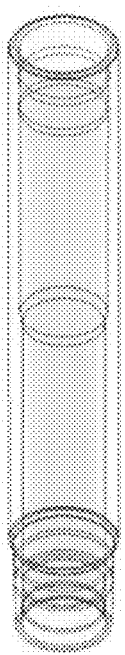
FIG. 2A illustrates a schematic perspective view of an exemplary embodiment of a centerband according to the present invention.
Figure 2B:
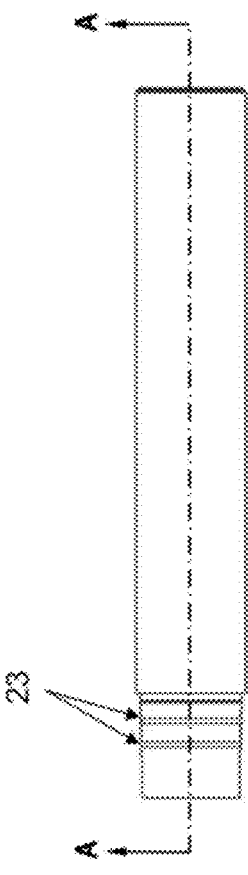
FIG. 2B illustrates a schematic side view of the exemplary embodiment of FIG. 2A.
Figure 2C:
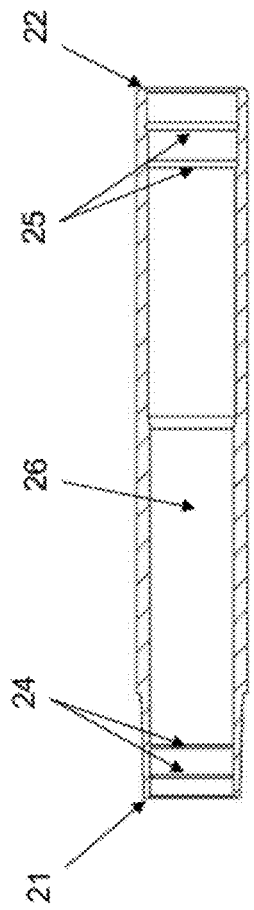
FIG. 2C illustrates a schematic cross-sectional view taken along line A-A shown in FIG. 2B of the exemplary embodiment of FIG. 2B.
Figure 2E:
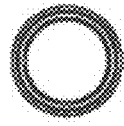
FIG. 2E illustrates a schematic bottom view of the exemplary embodiment of FIG. 2A.
Figure 2D:
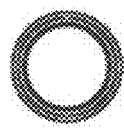
FIG. 2D illustrates a schematic top view of the exemplary embodiment of FIG. 2A.

FIGS. 1A to 1E illustrate an exemplary embodiment of an assembled click pen applicator device 10 according to the present invention. FIGS. 1F to 1J illustrate another exemplary embodiment of an assembled click pen applicator device 10' according to the present invention. Similar features among the exemplary embodiments are illustrated with like reference numerals.

The device 10, 10' may include three sections: an applicator section 11 at a distal end, a storage section 12 in a middle section, and a multistage actuator section 13 at a proximal end. The applicator section 11 may include a passing seat 30, 30', 30", a sealing element 40, an orifice reducer 50, 50', a nose 60, 60', 60", 60''', 60'''', and a cap 70, 70', the applicator section 11 configured to connect to a distal end of a centerband 20, 20'. The storage section 12 may be defined by a middle section of the centerband 20, 20'. The multistage actuator section 13 may include a piston seat 80, a cup 90, a sealing element 40, a spiral 100, a priming spring 110, a gear 120, a click spring 130, a spiral sleeve 140, and a push button 150, the multistage actuator section 13 configured to connect to a proximal end of the centerband 20, 20'. In the exemplary embodiment of FIGS. 1A to 1E, the cap 70 may be a push-on cap, whereas in the exemplary embodiment of FIGS. 1F to 1J, the cap 70' may be a screw-on cap. Further, the distal end of centerband 20, 20' of device 10, 10' may increase in diameter to match the diameter of the proximal end of the cap 70, 70'.

FIGS. 2A to 2E illustrate an exemplary embodiment of a centerband 20 defining a storage section 12 in the middle section of the device 10 according to the present invention. FIGS. 2F to 2J illustrate another exemplary embodiment of a centerband 20' defining a storage section 12 in the middle section of the device 10' according to the present invention. The applicator section 11 is configured to connect to a distal end 21 of a centerband 20, 20', and the multistage actuator section 13 configured to connect to a proximal end 22 of the centerband 20, 20'. Similar features among the exemplary embodiments are illustrated with like reference numerals.

The centerband 20, 20' defining the storage section 12 of the device 10, 10' may include a distal end 21 and a proximal end 22. The centerband 20, 20' may be in the shape of an elongate tube, pipe, barrel, or other similar shape defining a storage chamber 26 in its middle section configured to store and dispense a formulation. The distal end 21 of the centerband 20, 20' may include internal grooves 24 configured to interface with components of the applicator section 11. For example, the internal grooves 24 may interface with a passing seat 30, 30', 30" of the applicator section 11. In addition, the proximal end 22 of the centerband 20, 20' may include internal grooves 25 configured to interface with components of the multistage actuator section 13. For example, the internal grooves 25 may interface with a spiral sleeve 140 of the multistage actuator section 13. Alternatively, the centerband 20, 20' may include threads instead of external ribs 23, internal grooves 24, and/or internal grooves 25 for attachment to each of the applicator section 11 and the multistage actuator section 13.

In the exemplary embodiment of FIGS. 2A to 2E, the distal end 21 of the centerband 20 may include external ribs 23 configured to interface with components of the applicator section 11. For example, the external ribs 23 may interface with a cap 70 of the applicator section 11, the cap 70 being a push-on cap. In the exemplary embodiment of FIGS. 2F to 2J, the distal end 21 of the centerband 20' may include a flared outer surface 27 configured to abut against a proximal end of the cap 70, 70', which cap 70, 70' may be engaged or threaded to the passing seat 30, 30', 30".

The centerband 20, 20' may be made of polypropylene, polyethylene, and other suitable materials. Preferably, the centerband 20, 20' is made of polypropylene. In addition, the materials may be chosen based on the particular application and requirements of the device 10, 10', as well as the particular formulation that is to be dispensed. Further, the centerband 20, 20' may be manufactured by injection molding, or other suitable processes. Preferably, the centerband 20, 20' is manufactured by injection molding.

Figures 3A, 3B, 3C, 3D, 3E:
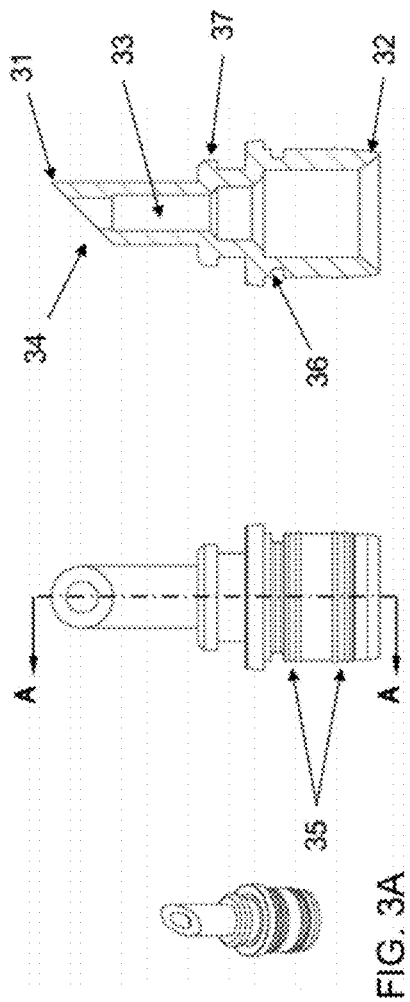
FIG. 3A illustrates a schematic perspective view of an exemplary embodiment of a passing seat according to the present invention.
FIG. 3B illustrates a schematic side view of the exemplary embodiment of FIG. 3A.
FIG. 3C illustrates a schematic cross-sectional view taken along line A-A shown in FIG. 3B of the exemplary embodiment of FIG. 3B.
FIG. 3D illustrates a schematic top view of the exemplary embodiment of FIG. 3A.
FIG. 3E illustrates a schematic bottom view of the exemplary embodiment of FIG. 3A.
Figure 3I:
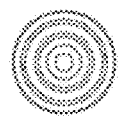
FIG. 3I illustrates a schematic top view of the exemplary embodiment of FIG. 3F.
Figure 3H:
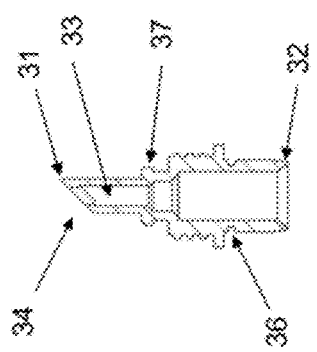
FIG. 3H illustrates a schematic cross-sectional view taken along line A-A shown in FIG. 3G of the exemplary embodiment of FIG. 3G.
Figure 3G:
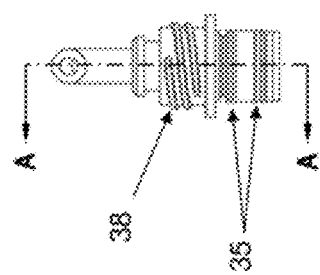
FIG. 3G illustrates a schematic side view of the exemplary embodiment of FIG. 3F.
Figure 3F:
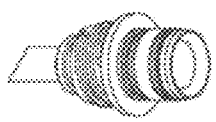
FIG. 3F illustrates a schematic perspective view of another exemplary embodiment of a passing seat according to the present invention.
Figure 3J:
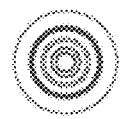
FIG. 3J illustrates a schematic bottom view of the exemplary embodiment of FIG. 3F.
Figure 3K:
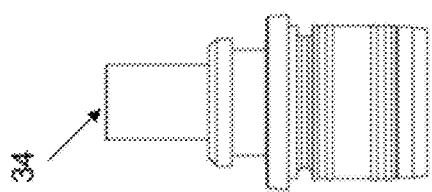
FIG. 3K illustrates a schematic side view of yet another exemplary embodiment of a passing seat according to the present invention.

FIGS. 3A to 3E illustrate an exemplary embodiment of a passing seat 30 in an applicator section 11 of the device 10 according to the present invention. FIGS. 3F to 3J illustrate another exemplary embodiment of a passing seat 30' in an applicator section 11 of the device 10' according to the present invention. FIG. 3K illustrates yet another exemplary embodiment of a passing seat 30" according to the present invention. Similar features among the exemplary embodiments are illustrated with like reference numerals.

The passing seat 30, 30', 30" in the applicator section 11 of the device 10, 10' may include a distal end 31 and a proximal end 32. The passing seat 30, 30', 30" may include a central passage 33 over its entire length, which central passage 33 may be in communication with the storage chamber 26 of the centerband 20, 20'. The distal end 31 of the passing seat 30, 30' may include an angled end face 34. However, other end faces may also be possible, such as flat, curved, rounded, convex, concave, and others. For example, FIG. 3K shows a passing seat 30" having a flat end face 34. The proximal end 32 of the passing seat 30, 30', 30" may include external ribs 35 configured to interface with the distal end 21 of the centerband 20, 20'. For example, the external ribs 35 of the passing seat 30, 30', 30" may interface with the internal grooves 24 of the centerband 20, 20'. Alternatively, the passing seat 30, 30', 30" may include threads instead of external ribs 35 for attachment to the centerband 20, 20'. In addition, the proximal end 32 of the passing seat 30, 30', 30" may include an annular groove 36 configured to receive a sealing element of the applicator section 11. For example, the annular groove 36 may receive a sealing element 40 that may seal the interface between the passing seat 30, 30', 30" of the applicator section 11 and the distal end 21 of the centerband 20, 20'. Further, the passing seat 30, 30', 30" may include an annular flange 37 configured to interface with a nose 60, 60', 60", 60"', 60"" of the applicator section 11. Alternatively, the passing seat 30, 30', 30" may include threads instead of the annular flange 37 for attachment to the nose 60, 60', 60", 60"', 60"" of the applicator section 11.

In the exemplary embodiment of FIGS. 3F to 3J, the passing seat 30' may also include threads 38 between the annular groove 36 and the annular flange 37 configured to engage with a threaded cap 70'.

The passing seat 30, 30', 30" may be made of polypropylene, polyethylene, and other suitable materials. Preferably, the passing seat 30, 30', 30" is made of polypropylene. In addition, the materials may be chosen based on the particular application and requirements of the device 10, 10', as well as the particular formulation that is to be dispensed. Further, the passing seat 30, 30', 30" may be manufactured by injection molding, or other suitable processes. Preferably, the passing seat 30, 30', 30" is manufactured by injection molding.

Figure 4A:
FIG. 4A illustrates a schematic perspective view of an exemplary embodiment of a sealing element according to the present invention.
Figure 4B:
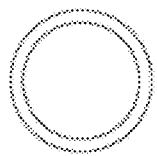
FIG. 4B illustrates a schematic top view of the exemplary embodiment of FIG. 4A.
Figure 4C:
FIG. 4C illustrates a schematic side view of the exemplary embodiment of FIG. 4A.
Figure 6M:
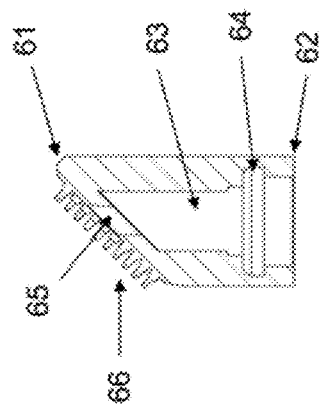
FIG. 6M illustrates a schematic cross-sectional view taken along line A-A shown in FIG. 6L of the exemplary embodiment of FIG. 6L.
Figure 6N:
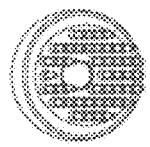
FIG. 6N illustrates a schematic top view of the exemplary embodiment of FIG. 6K.
Figure 6L:
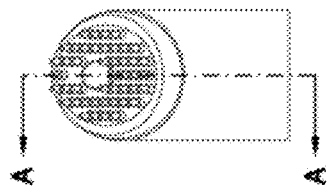
FIG. 6L illustrates a schematic side view of the exemplary embodiment of FIG. 6K.
Figure 6O:
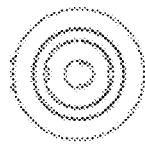
FIG. 6O illustrates a schematic bottom view of the exemplary embodiment of FIG. 6K.
Figure 6K:
FIG. 6K illustrates a schematic perspective view of yet another exemplary embodiment of a nose according to the present invention.
Figure 6R:
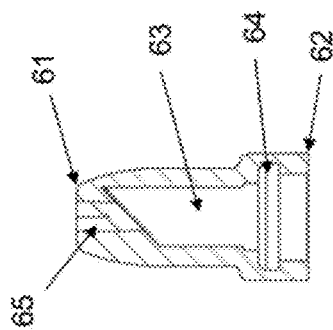
FIG. 6R illustrates a schematic cross-sectional view taken along line A-A shown in FIG. 6Q of the exemplary embodiment of FIG. 6Q.
Figure 6S:
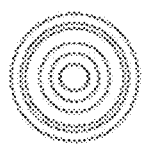
FIG. 6S illustrates a schematic top view of the exemplary embodiment of FIG. 6P.
Figure 6Q:
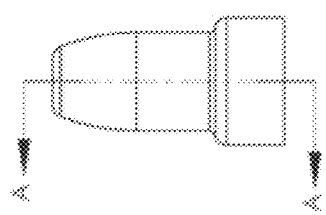
FIG. 6Q illustrates a schematic side view of the exemplary embodiment of FIG. 6P.
Figure 6T:
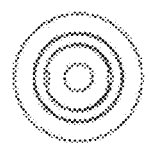
FIG. 6T illustrates a schematic bottom view of the exemplary embodiment of FIG. 6P.
Figure 6P:
FIG. 6P illustrates a schematic perspective view of yet another exemplary embodiment of a nose according to the present invention.
Figure 7C:
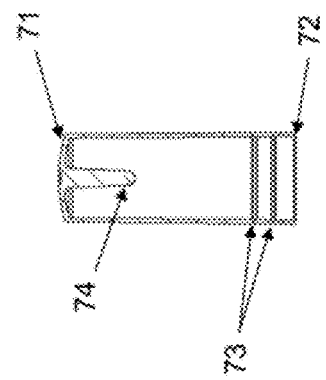
FIG. 7C illustrates a schematic cross-sectional view taken along line A-A shown in FIG. 7B of the exemplary embodiment of FIG. 7B.
Figure 7D:
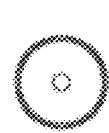
FIG. 7D illustrates a schematic top view of the exemplary embodiment of FIG. 7A.
Figure 7B:
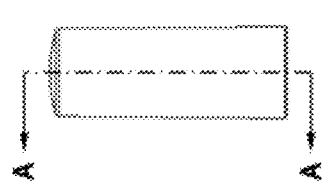
FIG. 7B illustrates a schematic side view of the exemplary embodiment of FIG. 7A.
Figure 7E:
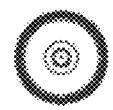
FIG. 7E illustrates a schematic bottom view of the exemplary embodiment of FIG. 7A.
Figure 7A:
FIG. 7A illustrates a schematic perspective view of an exemplary embodiment of a cap according to the present invention.

FIGS. 4A to 4C illustrate an exemplary embodiment of a sealing element 40 in an applicator section 11 of the device 10, 10' according to the present invention.

The sealing element 40 in the applicator section 11 of the device 10, 10' may include a circular o-ring configured and sized to fit within the annular groove 36 of the passing seat 30, 30', 30". The sealing element 40 may seal the interface between the passing seat 30, 30', 30" and the centerband 20, 20'.

The sealing element 40 may be made of rubber, thermoplastic rubber, silicone, and other suitable materials. Preferably, the sealing element 40 is made of rubber. In addition, the materials may be chosen based on the particular application and requirements of the device 10, 10', as well as the particular formulation that is to be dispensed. Further, the sealing element 40 may be manufactured by injection molding, compression molding, or other suitable processes. Preferably, the sealing element 40 is manufactured by compression molding.

FIGS. 5A to 5E illustrate an exemplary embodiment of an orifice reducer 50 in an applicator section 11 of the device 10 according to the present invention. FIGS. 5F to 5J illustrate another exemplary embodiment of an orifice reducer 50' in an applicator section 11 of the device 10' according to the present invention. Similar features among the exemplary embodiments are illustrated with like reference numerals.

The orifice reducer 50, 50' in the applicator section 11 of the device 10, 10' may include a distal end 51 and a proximal end 52. The orifice reducer 50, 50' may include a central passage 53 over its entire length, which central passage 53 may be in communication with the central passage 33 of the passing seat 30, 30', 30" and also with the storage chamber 26 of the centerband 20, 20'. The external shape of the orifice reducer 50, 50' may be configured to fit within the central passage 33 of the passing seat 30, 30', 30", thereby taking up at least part of the volume of the central passage 33 of the passing seat 30, 30', 30". In addition, the orifice reducer 50, 50' may include external ribs 54 configured to secure the orifice reducer 50, 50' within the central passage 33 of the passing seat 30, 30', 30". Alternatively, the orifice reducer 50, 50' may include threads instead of external ribs 54 for attachment to the passing seat 30, 30', 30". Further, in an alternative embodiment, the orifice reducer 50, 50' and the passing seat 30, 30', 30" may be manufactured as a single integral part, thereby potentially resulting in cost and time savings due to the elimination of both a part and an assembly step.

In the exemplary embodiment of FIGS. 5F to 5J, the orifice reducer 50' may be configured to fit within the central passage 33 of the passing seat 30' of FIGS. 3F to 3J, which passing seat 30' is configured to receive a threaded cap 70' on threads 38.

The orifice reducer 50, 50' may be made of polypropylene, polyethylene, and other suitable materials. Preferably, the orifice reducer 50, 50' is made of polypropylene. In addition, the materials may be chosen based on the particular application and requirements of the device 10, 10', as well as the particular formulation that is to be dispensed. Further, the orifice reducer 50, 50' may be manufactured by injection molding, or other suitable processes. Preferably, the orifice reducer 50, 50' is manufactured by injection molding.

FIGS. 6A to 6E illustrate an exemplary embodiment of a nose 60 in an applicator section 11 of the device 10, 10' according to the present invention. FIGS. 6F to 6J, 6K to 6O, 6P to 6T, and 6U to 6Y illustrate alternative exemplary embodiments of a nose 60', 60", 60"', 60"" in an applicator section 11 of the device 10, 10' according to the present invention. Similar features among the exemplary embodiments are illustrated with like reference numerals.

The nose 60, 60', 60'', 60''', 60'''' in the applicator section 11 of the device 10, 10' may include a distal end 61 and a proximal end 62. The nose 60, 60', 60'', 60''', 60'''' may include a central passage 63 over its entire length. The proximal end 62 of the nose 60, 60', 60'', 60''', 60'''' may be configured to receive the passing seat 30, 30', 30'' in the central passage 63. For example, the central passage 63 may include an annular groove 64 configured to interface with the annular flange 37 of the passing seat 30, 30', 30'', thereby securing the nose 60, 60', 60'', 60''', 60'''' to the passing seat 30, 30', 30''. Alternatively, the nose 60, 60', 60'', 60''', 60'''' may include threads instead of the annular groove 64 for attachment to the passing seat 30, 30', 30''. The distal end 61 of the nose 60, 60', 60'', 60''', 60'''' may include an orifice 65, which orifice 65 may be in communication with the central passage 33 of the passing seat 30, 30', 30'', with the central passage 53 of the orifice reducer 50, 50', and also with the storage chamber 26 of the centerband 20, 20'. The orifice 65 may be sized to dispense a formulation for application by a user. In addition, the distal end 61 of the nose 60, 60', 60'', 60''', 60'''' may include brushes 66 to facilitate application and/or spreading of the formulation by a user.

The nose 60 as shown in FIGS. 6A to 6E includes a shape that tapers towards the distal end 61 of the nose 60. Other shapes of the nose 60 may be possible. For example, FIGS. 6F to 6J, 6K to 6O, 6P to 6T, and 6U to 6Y illustrate alternative exemplary embodiments of a nose 60', 60'', 60''', 60'''' in an applicator section 11 of the device 10, 10', in which the nose 60', 60'', 60''', 60'''' may include a stepped cylindrical shape, a cylindrical shape, or a tapered and stepped cylindrical shape. Additionally, other shapes may be possible. Further, alternative exemplary embodiments may include different end faces, such as angled, flat, curved, rounded, convex, concave, and others, end faces with or without brushes 66, and/or end faces including antimicrobial additives or substances, and alternative exemplary embodiments may be configured to receive passing seats 30, 30', 30'' having variously shaped end faces 34, as described above. Moreover, in an alternative embodiment, the nose 60, 60', 60'', 60''', 60'''' and the passing seat 30, 30', 30'', and possibly the orifice reducer 50, 50', may be manufactured as a single integral part, thereby potentially resulting in cost and time savings due to the elimination of both a part and an assembly step.

The nose 60, 60', 60'', 60''', 60'''' may be made of polyethylene, rubber, thermoplastic rubber, silicone, and other suitable materials. Preferably, the nose 60, 60', 60'', 60''', 60'''' is made of rubber. In addition, the materials may be chosen based on the particular application and requirements of the device 10, 10', as well as the particular formulation that is to be dispensed. Further, the nose 60, 60', 60'', 60''', 60'''' may be manufactured by injection molding, compression molding, or other suitable processes. Preferably, the nose 60, 60', 60'', 60''', 60'''' is manufactured by compression molding.

FIGS. 7A to 7E illustrate an exemplary embodiment of a cap 70 in an applicator section 11 of the device 10 according to the present invention. FIGS. 7F to 7J illustrate another exemplary embodiment of a cap 70' in an applicator section 11 of the device 10' according to the present invention. Similar features among the exemplary embodiments are illustrated with like reference numerals.

The cap 70, 70' in the applicator section 11 of the device 10, 10' may include a distal end 71 and a proximal end 72. The cap 70, 70' may be sized to fit over the passing seat 30, 30', 30'' and nose 60, 60', 60'', 60''', 60'''' of the applicator section 11. The distal end 71 of the cap 70, 70' may include a pintel 74 configured to seal the orifice 65 of the nose 60, 60', 60'', 60''', 60''''. For example, the pintel 74 of the cap 70, 70' may be sized to fit snugly within and extend for a short distance into the orifice 65 of the nose 60, 60', 60'', 60''', 60'''', thereby sealing the orifice 65 when the device 10, 10' is not in use. Moreover, the cap 70, 70' may also include a tamper-resistant feature, not shown, to indicate whether a product has been previously used. The cap 70, 70' may also include features on its external surface to facilitate grasping, pulling, pushing, twisting, or otherwise manipulating the cap 70, 70', such as, for example, ribs, grooves, indentations, gripping pads or surfaces, rubberized portions, and other similar features.

In the exemplary embodiment of FIGS. 7A to 7E, the proximal end 72 of the cap 70 may include internal grooves 73 configured to interface with the distal end 21 of the centerband 20 of the device 10. For example, the internal grooves 73 of the cap 70 may interface with the external ribs 23 of the centerband 20 of FIGS. 2A to 2E, thereby protecting the applicator section 11, in particular, the nose 60, 60', 60'', 60''', 60'''' and brushes 66, when not in use. In the exemplary embodiment of FIGS. 7F to 7J, the proximal end 72 of the cap 70' may include threads 75, instead of internal grooves 73, configured to interface with threads 38 of the passing seat 30' of FIGS. 3F to 3J, thereby protecting the applicator section 11, in particular, the nose 60, 60', 60'', 60''', 60'''' and brushes 66, when not in use.

The cap 70, 70' may be made of polypropylene, polyethylene, acrylonitrile butadiene styrene, styrene acrylonitrile, and other suitable materials. Preferably, the cap 70, 70' is made of polypropylene. In addition, the materials may be chosen based on the particular application and requirements of the device 10, 10', as well as the particular formulation that is to be dispensed. Further, the cap 70, 70' may be manufactured by injection molding, or other suitable processes. Preferably, the cap 70, 70' is manufactured by injection molding.

FIGS. 8A to 8E illustrate an exemplary embodiment of a piston seat 80 in a multistage actuator section 13 of the device 10, 10' according to the present invention.

The piston seat 80 in the multistage actuator section 13 of the device 10, 10' may include a distal end 81 and a proximal end 82. The piston seat 80 may include a shaft 83 having at least one thread 84, and a support member 85 at the distal end 81 of the shaft 83. The support member 85 at the distal end 81 may include an external rib 86 and a piston seat flange 87 configured to receive a cup that contacts the formulation to be dispensed. For example, the external rib 86 and the piston seat flange 87 may interface with a cup 90 that supports and advances the formulation. The shaft 83 may include a priming threaded portion 84a at the distal end 81 of the piston seat 80 adjacent to the support member 85, an unthreaded portion 88 proximal to the priming threaded portion 84a, and a dosing threaded portion 84b that extends substantially the remaining length of the shaft 83 from the unthreaded portion 88 to the proximal end 82 of the shaft 83. The priming threaded portion 84a and the dosing threaded portion 84b may be configured to engage a spiral 100. The priming threaded portion 84a and the dosing threaded portion 84b may have the same pitch. Alternatively, the pitch of the priming threaded portion 84a may be a multiple of, for example, double, the pitch of the dosing threaded portion 84b. The priming threaded portion 84a may include only one turn of threads, preferably a three-quarter turn or a half turn. The axial length of the unthreaded portion 88 may be sized to displace a predetermined volume within the storage section 12. The pitch of the dosing threaded portion 84b may be sized to dispense a predetermined dose, or other predetermined amount, of the formulation with each actuation of the multistage actuator section 13. The shaft 83 may include a keyed shape configured to interface with a gear 120. For example, the shaft 83 may include at least one flat surface 89, and preferably two diametrically opposed flat surfaces 89, extending the length of the shaft 83. As a result of the keyed shape of the shaft 83, the threads 84 of the priming threaded portion 84a and the dosing threaded portion 84b may be discontinuous around a perimeter of the shaft. That is, the at least one flat surface 89 may be substantially free of threads.

The piston seat 80 may be made of polyoxymethylene, and other suitable materials. Preferably, the piston seat 80 is made of polyoxymethylene. In addition, the materials may be chosen based on the particular application and requirements of the device 10, 10', as well as the particular formulation that is to be dispensed. Further, the piston seat 80 may be manufactured by injection molding, or other suitable processes. Preferably, the piston seat 80 is manufactured by injection molding.

FIGS. 9A to 9E illustrate an exemplary embodiment of a cup 90 in a multistage actuator section 13 of the device 10, 10' according to the present invention.

The cup 90 in the multistage actuator section 13 of the device 10, 10' may include a distal end 91 and a proximal end 92. The distal end 91 of the cup 90 may be configured to support and advance a formulation stored in the storage chamber 26 of the centerband 20, 20'. The proximal end 92 of the cup 90 may include an internal groove 93 configured to interface with the piston seat 80. For example, the internal groove 93 of the cup 90 may interface with the external rib 86 of the piston seat 80, thereby securing the cup 90 to the distal end 81 of the piston seat 80. Further, the cup 90 may include an annular groove 94 configured to receive a sealing element of the multistage actuator section 13. For example, the annular groove 94 may receive a sealing element 40 that is configured and sized to seal the interface between the cup 90 of the multistage actuator section 13 and the proximal end 22 of the centerband 20, 20'. Further, in an alternative embodiment, the cup 90 and the piston seat 80 may be manufactured as a single integral part, thereby potentially resulting in cost and time savings due to the elimination of both a part and an assembly step.

The cup 90 may be made of polypropylene, polyethylene, and other suitable materials. Preferably, the cup 90 is made of polypropylene. In addition, the materials may be chosen based on the particular application and requirements of the device 10, 10', as well as the particular formulation that is to be dispensed. Further, the cup 90 may be manufactured by injection molding, or other suitable processes. Preferably, the cup 90 is manufactured by injection molding.

FIGS. 10A to 10E illustrate an exemplary embodiment of a spiral 100 in a multistage actuator section 13 of the device 10, 10' according to the present invention.

The spiral 100 in the multistage actuator section 13 of the device 10, 10' may include a distal end 101 and a proximal end 102. The spiral 100 may include a central passage 103 over its entire length, through which the shaft 83 of the piston seat 80 may extend. A portion of the central passage 103 may also include internal threads 104 configured to engage the priming threaded portion 84a and the dosing threaded portion 84b of the shaft 83 of the piston seat 80. The distal end 101 of the spiral 100 may include an annular channel 105 configured to receive a spring element. For example, the annular channel 105 of the spiral 100 may receive a proximal end of a priming spring 110. Further, the proximal end 102 of the spiral 100 may include an annular channel 106 also configured to received a spring element. For example, the annular channel 106 of the spiral 100 may receive a distal end of a click spring 130. In addition, the proximal end 102 of the spiral 100 may include at least one snap element 107, preferably two diametrically opposed snap elements 107, configured to engage a spiral sleeve 140, thereby securing the spiral 100 to the spiral sleeve 140.

The spiral 100 may be made of polyoxymethylene, and other suitable materials. Preferably, the spiral 100 is made of polyoxymethylene. In addition, the materials may be chosen based on the particular application and requirements of the device 10, 10', as well as the particular formulation that is to be dispensed. Further, the spiral 100 may be manufactured by injection molding, or other suitable processes. Preferably, the spiral 100 is manufactured by injection molding.

FIGS. 11A to 11C illustrate an exemplary embodiment of a priming spring 110 in a multistage actuator section 13 of the device 10, 10' according to the present invention.

The priming spring 110 in the multistage actuator section 13 of the device 10, 10' may include a distal end 111 and a proximal end 112. The priming spring 110 may be situated over a length of the shaft 83 of the piston seat 80. For example, the priming spring 110 may be situated substantially over the unthreaded portion 88 of the shaft 83. The distal end 111 of the priming spring 110 may abut against a proximal surface of the piston seat flange 87 of the piston seat 80, and the proximal end 112 of the priming spring 110 may be received in the annular channel 105 of the spiral 100. The priming spring 110 may be configured to apply force between the piston seat 80 and the spiral 100, such that the piston seat 80 is pushed in a distal direction and the spiral 100 is pushed in a proximal direction. The spring rate of the priming spring 110 may be configured to expand over a length of the unthreaded portion 88 of the shaft 83, thereby displacing a predetermined volume within the storage chamber 26 of the centerband 20, 20' when the piston seat 80 is rotated by the click mechanism such that the internal threads 104 of the spiral 100 disengage the priming threaded portion 84a and the priming spring 110 advances the piston seat 80 over the length of the unthreaded portion 88 of the shaft 83.

The priming spring 110 may be made of steel, and other suitable materials. Preferably, the priming spring 110 is made of steel. In addition, the materials may be chosen based on the particular application and requirements of the device 10, 10', as well as the particular formulation that is to be dispensed. Further, the priming spring 110 may be manufactured by coiling, or other suitable processes. Preferably, the priming spring 110 is manufactured by coiling.

FIGS. 12A to 12E illustrate an exemplary embodiment of a gear 120 in a multistage actuator section 13 of the device 10, 10' according to the present invention.

The gear 120 in the multistage actuator section 13 of the device 10, 10' may include a distal end 121 and a proximal end 122. The gear 120 may include a central passage 123 over its entire length, through which the shaft 83 of the piston seat 80 may at least partially extend. A portion of the central passage 123 may also include a keyed shape configured to interface with the shaft 83 of the piston seat 80. For example, the central passage 123 of the gear 120 may include at least one flat surface 124, preferably two diametrically opposed flat surfaces 124, configured to engage with the shaft 83. For example, the at least one flat surface 124 of the gear 120 may engage the at least one flat surface 89 of the shaft 83 of the piston seat 80. In addition, the gear 120 may include a flange 125 configured to engage with a spring element. For example, the flange 125 of the gear 120 may engage a proximal end of a click spring 130. The gear 120 may also include angled teeth 126 facing the proximal end 122 of the gear 120, which angled teeth 126 may be configured to engage with a spiral sleeve 140 and a push button 150.

The gear 120 may be made of polyoxymethylene, and other suitable materials. Preferably, the gear 120 is made of polyoxymethylene. In addition, the materials may be chosen based on the particular application and requirements of the device 10, 10', as well as the particular formulation that is to be dispensed. Further, the gear 120 may be manufactured by injection molding, or other suitable processes. Preferably, the gear 120 is manufactured by injection molding.

Figure 13A:
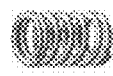
FIG. 13A illustrates a schematic perspective view of an exemplary embodiment of a click spring according to the present invention.
Figure 13B:
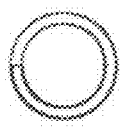
FIG. 13B illustrates a schematic top view of the exemplary embodiment of FIG. 13A.
Figure 13C:
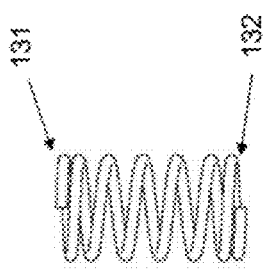
FIG. 13C illustrates a schematic side view of the exemplary embodiment of FIG. 13A.
Figures 14A, 14B, 14C, 14D, 14E:
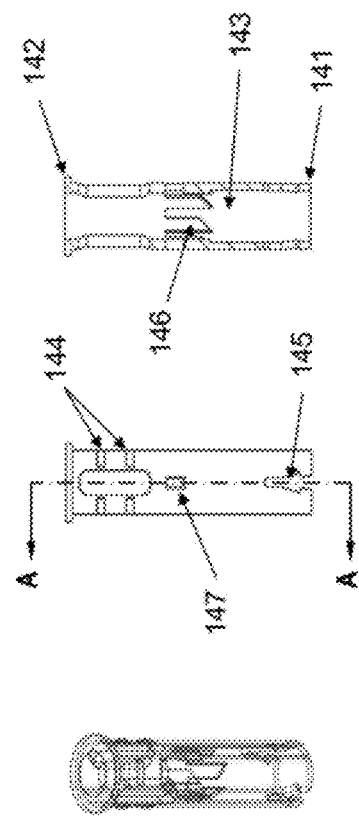
FIG. 14A illustrates a schematic perspective view of an exemplary embodiment of a spiral sleeve according to the present invention.
FIG. 14B illustrates a schematic side view of the exemplary embodiment of FIG. 14A.
FIG. 14C illustrates a schematic cross-sectional view taken along line A-A shown in FIG. 14B of the exemplary embodiment of FIG. 14B.
FIG. 14D illustrates a schematic top view of the exemplary embodiment of FIG. 14A.
FIG. 14E illustrates a schematic bottom view of the exemplary embodiment of FIG. 14A.

FIGS. 13A to 13C illustrate an exemplary embodiment of a click spring 130 in a multistage actuator section 13 of the device 10, 10' according to the present invention.

The click spring 130 in the multistage actuator section 13 of the device 10, 10' may include a distal end 131 and a proximal end 132. The click spring 130 may be situated over a length of the shaft 83 of the piston seat 80, and over a distal end 121 of the gear 120. The distal end 131 of the click spring 130 may be received in the annular channel 106 of the spiral 100, and the proximal end 132 of the click spring 130 may abut against a distal surface of the flange 125 of the gear 120. The click spring 130 may be configured to apply force between the spiral 100 and the gear 120, such that the spiral 100 is pushed in a distal direction and the gear 120 is pushed in a proximal direction. The spring rate of the click spring 130 may be configured to provide for positive feedback during operation of the multistage actuator section 13.

The click spring 130 may be made of steel, and other suitable materials. Preferably, the click spring 130 is made of steel. In addition, the materials may be chosen based on the particular application and requirements of the device 10, 10', as well as the particular formulation that is to be dispensed. Further, the click spring 130 may be manufactured by coiling, or other suitable processes. Preferably, the click spring 130 is manufactured by coiling.

FIGS. 14A to 14E illustrate an exemplary embodiment of a spiral sleeve 140 in a multistage actuator section 13 of the device 10, 10' according to the present invention.

The spiral sleeve 140 in the multistage actuator section 13 of the device 10, 10' may include a distal end 141 and a proximal end 142. The spiral sleeve 140 may include a central cavity 143 over its entire length, inside of which the shaft 83 of the piston seat 80, the spiral 100, the gear 120, the click spring 130, and a push button 150 may each be at least partially situated. The proximal end 142 of the spiral sleeve 140 may include external ribs 144 configured to engage with the centerband 20, 20'. For example, the external ribs 144 of the spiral sleeve 140 may engage the internal grooves 25 of the centerband 20, 20'. Alternatively, the spiral sleeve 140 may include threads instead of external ribs 144 for attachment to the proximal end 22 of the centerband 20, 20'. The distal end 141 of the spiral sleeve 140 may include at least one snap groove 145, preferably two diametrically opposed snap grooves 145, configured to receive the at least one snap element 107 of the spiral 100, thereby securing the spiral 100 to the spiral sleeve 140. Further, the spiral sleeve 140 may also include angled teeth 146 facing the distal end 141 of the spiral sleeve 140, which angled teeth 146 may be configured to engage with the angled teeth 126 of the gear 120. Moreover, the spiral sleeve 140 may also include at least one locking groove 147, preferably two diametrically opposed locking grooves 147, configured to receive at least one locking element of the push button 150.

The spiral sleeve 140 may be made of acrylonitrile butadiene styrene, styrene acrylonitrile, polyoxymethylene, and other suitable materials. Preferably, the spiral sleeve 140 is made of acrylonitrile butadiene styrene. In addition, the materials may be chosen based on the particular application and requirements of the device 10, 10', as well as the particular formulation that is to be dispensed. Further, the spiral sleeve 140 may be manufactured by injection molding, or other suitable processes. Preferably, the spiral sleeve 140 is manufactured by injection molding.

FIGS. 15A to 15E illustrate an exemplary embodiment of a push button 150 in a multistage actuator section 13 of the device 10, 10' according to the present invention.

The push button 150 in the multistage actuator section 13 of the device 10, 10' may include a distal end 151 and a proximal end 152. The push button 150 may include a central cavity 153, inside of which the shaft 83 of the piston seat 80 and the gear 120 may be at least partially situated. The distal end 151 of the push button 150 may include angled teeth 154 facing the distal end 151 of the push button 150, which angled teeth 154 may be configured to engage with the angled teeth 126 of the gear 120. Further, the push button 150 may also include at least one locking element 155, preferably two diametrically opposed locking elements 155, configured to engage at least one locking groove 147 of the spiral sleeve 140. Moreover, the proximal end 152 of the push button 150 may be configured to facilitate comfortable operation of the multistage actuator section 13 of the device 10, 10', and may include features on its external surface to facilitate grasping, pulling, pushing, twisting, or otherwise manipulating the cap 70, 70', such as, for example, ribs, grooves, indentations, gripping pads or surfaces, rubberized portions, and other similar features.

The push button 150 may be made of acrylonitrile butadiene styrene, styrene acrylonitrile, polyoxymethylene, and other suitable materials. Preferably, the push button 150 is made of acrylonitrile butadiene styrene. In addition, the materials may be chosen based on the particular application and requirements of the device 10, 10', as well as the particular formulation that is to be dispensed. Further, the push button 150 may be manufactured by injection molding, or other suitable processes. Preferably, the push button 150 is manufactured by injection molding.

Figure 16:
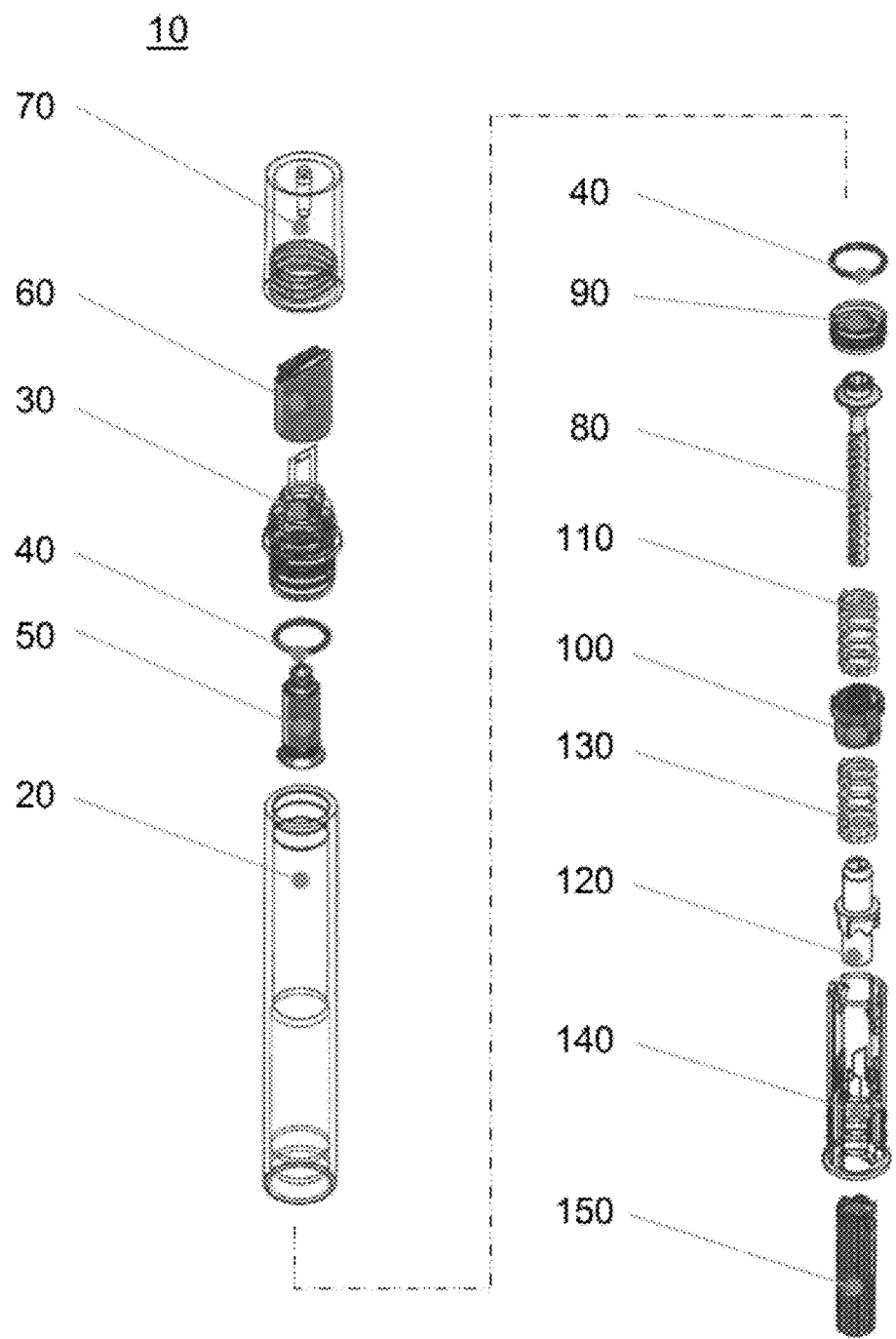
FIG. 16 illustrates a schematic perspective, exploded view of an exemplary embodiment of a click pen applicator device according to the present invention.
Figure 17:
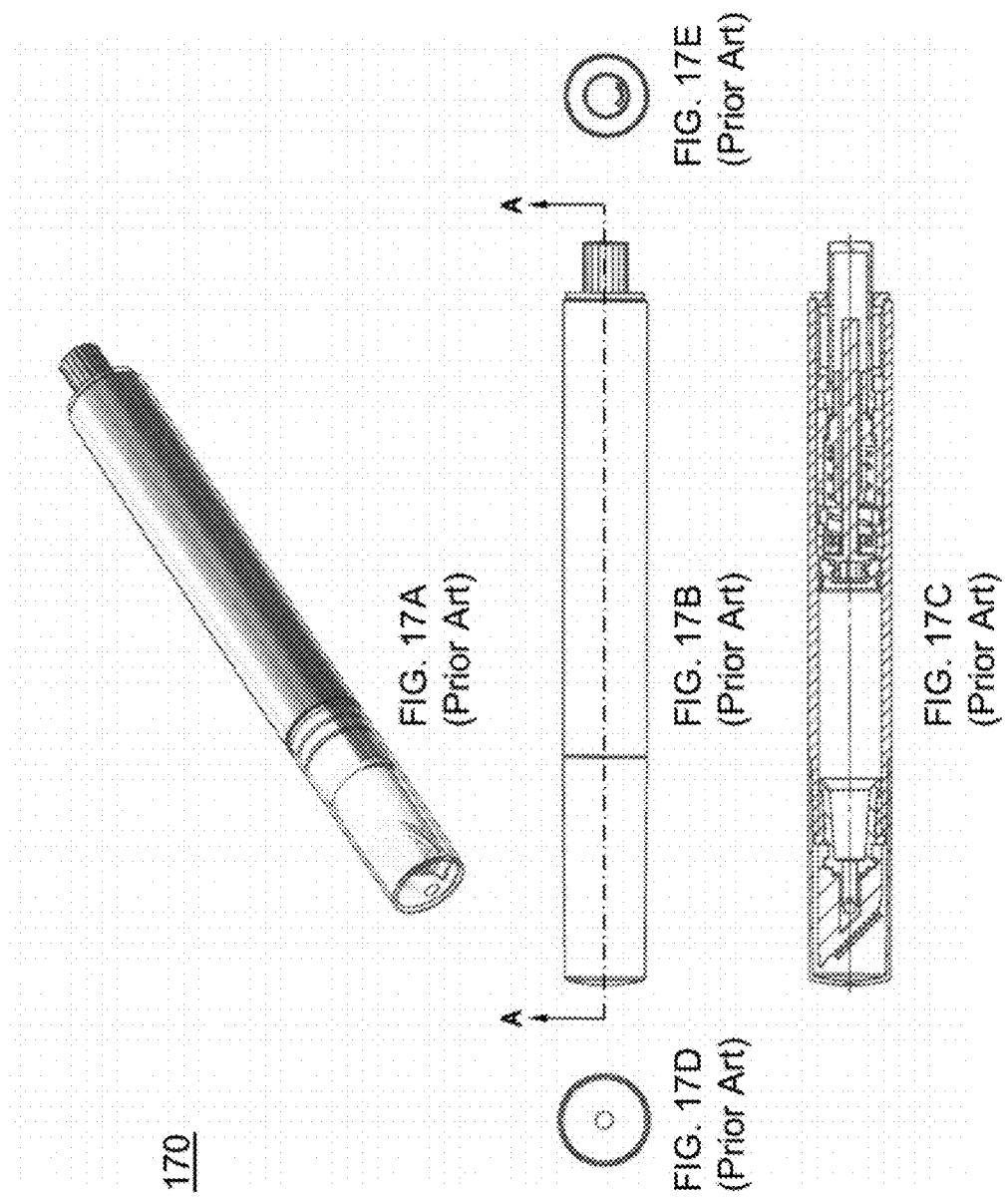
FIG. 17A illustrates a schematic perspective view of a prior art click pen applicator device.
FIG. 17B illustrates a schematic side view of the prior art click pen applicator device of FIG. 17A.
FIG. 17C illustrates a schematic cross-sectional view taken along line A-A shown in FIG. 17B of the prior art click pen applicator device of FIG. 17B.
Figure 18:
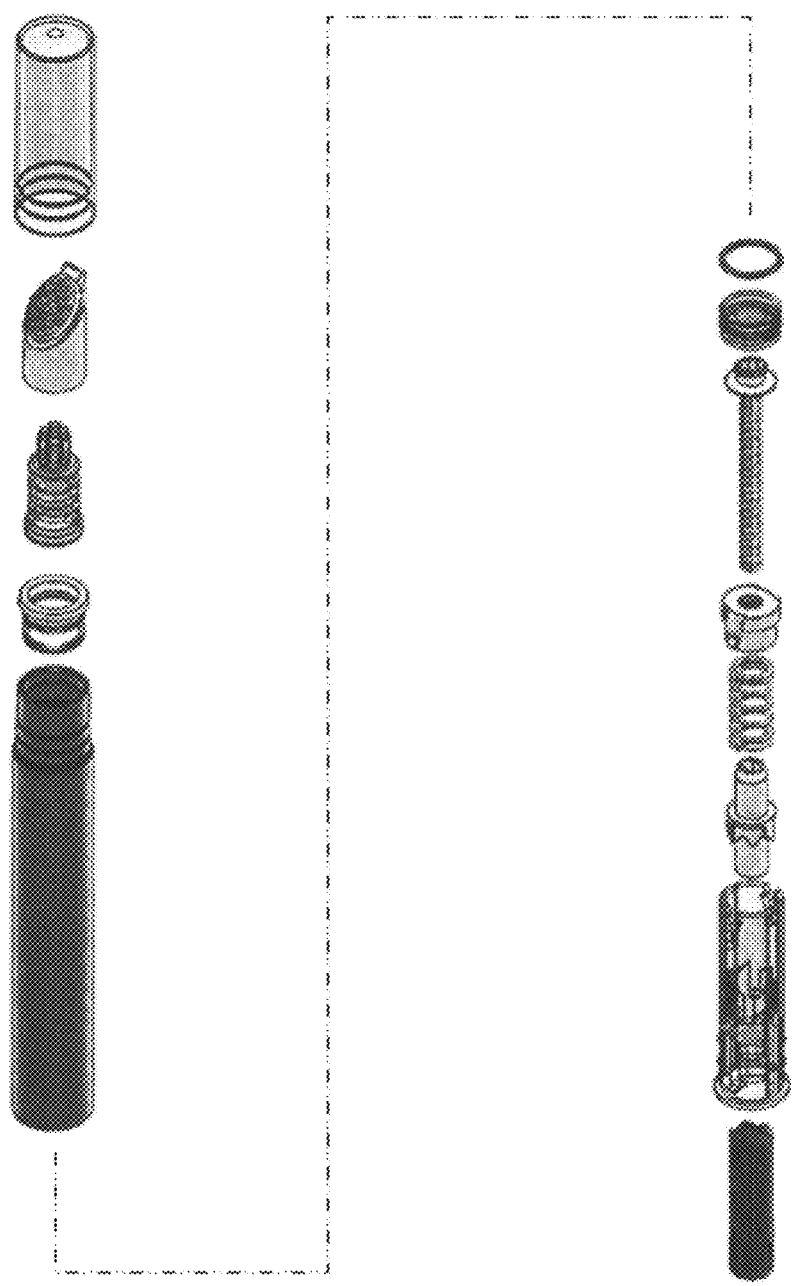

FIG. 16 illustrates an exploded view of an exemplary embodiment of a click pen applicator device 10, 10' according to the present invention.

In the foregoing description, it is understood that the particular descriptions of grooves of one component and ribs/elements of another component may be switched, such that ribs/elements may be provided in place of grooves, and vice versa. Further, it is understood that other connection mechanisms besides ribs and grooves, snap elements and grooves, locking elements and grooves, or threads, may be used to effect the interengagement of the various components of the device 10, 10', such as, for example, other mechanical engagement features, press-fitting, interference fitting, adhesive, and others.

The assembled click pen applicator device 10, 10' may be substantially airtight to prevent evaporation and/or weight loss of the formulation stored in the storage chamber 26 of the centerband 20, 20'. In this regard, the sealing element 40 situated in the annular groove 94 of the cup 90, the sealing element 40 situated in the annular groove 36 of the passing seat 30, 30', 30", and the pintel 74 of the cap 70, 70' may all contribute to the airtight sealing of the formulation in the storage chamber 26. In addition, the two sealing elements 40 may be the same or different sizes depending on the parts and interface to be sealed. Further, the device 10, 10' may also include tape around the outside of the cap 70, 70' to cover and/or seal the interface between the cap 70, 70' and the centerband 20, 20'. Moreover, the formulation stored in the storage chamber 26 of the centerband 20, 20' may also be provided in a bag, pouch, or similar container to further improve the airtight sealing of the formulation within the device 10, 10'.

The device 10, 10' may be hand assembled, which assembly may be facilitated by tools, jigs, and other suitable assembly aids. Alternatively, all or portions of the device 10, 10' may be assembled by an automated system.

A method of using the click pen applicator device 10, 10' according to the present invention may include the steps of priming the formulation at a priming rate, and dosing the formulation at a dosing rate. The click pen applicator device 10, 10' having a multistage actuator section 13 according to the present invention may allow for rapid priming using a click dosage mechanism.

In an initial, e.g., purchased, state of the device 10, 10', all components of the device 10, 10' are assembled. In the storage section 12, the storage chamber 26 of the centerband 20, 20' may be substantially filled with a formulation, e.g., a salicylic acid compound such as a wart remover formulation. In the applicator section 11, some of the formulation may contact the proximal end 52 of the orifice reducer 50, 50', and further, some of the formulation may be present within the central passage 53 of the orifice reducer 50, 50'. However, in order to prevent overflow and/or spillage during initial assembly of the device 10, 10' having the formulation in the storage chamber 26, an air gap may be present between the distal fill level of the formulation and the proximal end 52 of the orifice reducer 50, 50' in the initial, purchased state. In the multistage actuator section 13, the piston seat 80 and cup 90 may be in their most proximal position in the initial, purchased state of the device 10, 10'. That is, the priming threaded portion 84a may be engaged with the internal threads 104 of the spiral 100, thereby positioning the cup 90 in its most proximal position and also compressing the priming spring 110 between the piston seat 80 and the spiral 100.

Further, in the initial, purchased state of the device 10, 10', the push button 150 may be in its locked position, in which the push button 150 is rotated about a longitudinal axis of the device 10, 10' such that the at least one locking element 155 of the push button 150 may be received in the at least one locking groove 147 of the spiral sleeve 140. Before using the device 10, 10', if the push button 150 is in the locked position, the push button 150 may be rotated about the longitudinal axis of the device 10, 10' such that the at least one locking element 155 of the push button 150 is no longer received in the at least one locking groove 147 of the spiral sleeve 140.

The priming step prior to dosing of the formulation may allow the formulation to fill any air gaps and/or empty volume of the storage section 12 and/or the applicator section 11. For example, during the priming step, the formulation may fill in any air gap between the distal fill level in the storage chamber 26 and the proximal end 52 of the orifice reducer 50, 50'. In addition, the formulation may fill the empty volumes of the central passage 53 of the orifice reducer 50, 50' and substantially all of the central passage 33 of the passing seat 30, 30', 30''. Further, the formulation may also partially fill the empty volume of the orifice 65 of the nose 60, 60', 60'', 60''', 60''''. Thus, the priming step allows the formulation to be primed and ready for use by a user during the dosing step.

The priming step may be performed by the multistage actuator section 13 at a priming rate. The device 10, 10' may be primed from its initial, purchased state by pressing the push button 150 of the multistage actuator section 13, i.e., the click pen dosage mechanism. Each press of the push button 150 may move the piston seat 80 and the cup 90 in a distal direction at the rate of a dosing click, thereby advancing the formulation and filling some of the air gaps and/or empty volume in the storage section 12 and/or the applicator section 11 by a dosing amount. After a first actuation of the push button 150, the priming threaded portion 84a of the piston seat 80 may disengage from the internal threads 104 of the spiral 100. Due to the force of the priming spring 110 pushing the piston seat 80 in a distal direction away from the spiral 100, the piston seat 80 and the cup 90 may move in a distal direction after disengagement of the priming threaded portion 84a and the internal threads 104. In addition, after such disengagement of the priming threaded portion 84a, because the piston seat 80 includes an unthreaded portion 88 to which the internal threads 104 of the spiral 100 do not engage, the force of the priming spring 110 may advance the piston seat 80 and the cup 90 a distance substantially equivalent to the length of the unthreaded portion 88 of the piston seat 80, thereby effecting rapid priming of the formulation using the same click pen dosing mechanism. Thus, the disengagement of the priming threaded portion 84a and the rapid advancement of the piston seat 80 and the cup 90 under force of the priming spring 110 over the unthreaded length 88 of the piston seat 80 facilitates rapid filling of the air gaps and/or empty volume in the storage section 12 and/or the applicator section 11.

Accordingly, the priming step at the priming rate according to the present invention allows the device 10, 10' to be primed and ready for use by a user very quickly and efficiently. The first priming actuation may take up an empty volume of the device 10, 10' that would have normally required many, e.g., forty to seventy or more, individual actuations using a conventional actuating mechanism. However, the priming step according to the present invention is substantially transparent to the user because the user simply actuates the multistage actuating section 13 in a known manner, i.e., by pressing the push button 150. No additional or different steps or actuations are required by the user to effect rapid priming. The rapid priming also eliminates the possibility that a user may think a dispensing device is broken, non-functional, empty, dried up, or otherwise unusable due to the high number of required priming actuations before dosing of the formulation actually begins.

Although the above description refers to a first actuation of the priming step that leads to disengagement of the priming threaded portion 84a and the internal threads 104, the first actuation may include more than one actuation of the push button 150 before disengagement depending upon the number of threads in the priming threaded portion 84a and the rate of rotation of the click mechanism. Preferably, fewer than ten, and more preferably, only one or two, actuations of the push button 150 may be required to effect disengagement of the priming threaded portion 84a and the internal threads 104. The number of actuations required to effect such disengagement may depend on the length of the priming threaded portion 84a, for example, one turn of threads, preferably a three-quarter turn or a half turn.

Further, the priming rate may depend on the dimension of the unthreaded length 88 of the piston seat 80, the spring rate of the priming spring 110, the friction force of the sealing element 40, and/or the viscosity or other characteristics of the formulation. For example, the unthreaded length 88 of the piston seat 80 may be sized such that the air gaps and/or empty volume of the storage section 12 and/or the applicator section 11 may be substantially filled when the piston seat 80 and the cup 90 advance in a distal direction over the unthreaded length 88 of the piston seat 80. In addition, the spring rate of the priming spring 110 may be configured to provide sufficient force to advance the piston seat 80 and the cup 90, taking into consideration the friction force of the sealing element 40 engaged between the cup 90 and the centerband 20, 20', and the viscosity and other characteristics of the formulation.

After disengagement of the priming threaded portion 84a and the internal threads 104, and after advancement of the piston seat 80 and the cup 90 over an unthreaded length 88 of the piston seat 80, the dosing threaded portion 84b of the piston seat 80 may then engage the internal threads 104 of the spiral 100 upon further actuations of the push button 150. In order to fully effect priming of the device 10, 10' before the formulation is ready to be dispensed, the priming step may require one or more actuations of the push button 150 after engagement of the dosing threaded portion 84b with the internal threads 104, although it may be preferable that the device 10, 10' is ready to dispense the formulation without any such additional actuations.

The dosing step may be performed by the multistage actuator section 13 at a dosing rate. The formulation may be dosed with each actuation of the push button 150 after the dosing threaded portion 84b of the piston seat 80 has engaged the internal threads 104 of the spiral 100. Each press of the push button 150 may move the piston seat 80 and the cup 90 in a distal direction, thereby advancing and dispensing a predetermined dose of the formulation from the storage chamber 26 of the centerband 20, 20' through the central passage 53 of the orifice reducer 50, 50', through the central passage 33 of the passing seat 30, 30', 30", and out of the orifice 65 of the nose 60, 60', 60", 60"', 60"".

The dosing rate may depend on the pitch of the dosing threaded portion 84b of the piston seat 80 and the corresponding pitch of the internal threads 104 of the spiral 100. For example, the pitch of the dosing threaded portion 84b and the internal threads 104 may be configured such that a single actuation of the push button 150 dispenses a predetermined dose of the formulation from the nose 60, 60', 60", 60"', 60"".

Accordingly, the device 10, 10' according to the present invention allows for both rapid priming of the formulation for quick and reliable use after purchase, and also predetermined dosing of the formulation thereafter, while utilizing a click dosage mechanism with a multistage actuator section 13. Thus, the device 10, 10' drastically improves the priming rate of the device 10, 10' while simultaneously providing precise control of the dosing rate, but does so without complicating the steps for using the device 10, 10'.

When a user wishes to store the device 10, 10' after use, the device 10, 10' may be stored in an airtight manner to prevent evaporation and/or weight loss of the formulation, and may also be locked to prevent inadvertent or accidental dispensing of the formulation. In this regard, a cap 70, 70' may be placed over the passing seat 30, 30', 30" and nose 60, 60', 60", 60"', 60"" and engaged with the distal end 21 of the centerband 20, 20'. For airtight storage, the cap 70, 70' may include a pintel 74 that may be configured to fit snugly within and at least partially extend into the orifice 65 of the nose 60, 60', 60", 60"', 60"", and may at least partially extend into the central passage 33 of the passing seat 30, 30', 30". The cap 70, 70' may also protect the nose 60, 60', 60", 60"', 60"" and the brushes 66 from damage. For locking of the device 10, 10', the push button 150 may be rotated about a longitudinal axis of the device 10, 10' such that the at least one locking element 155 of the push button 150 may be received in the at least one locking groove 147 of the spiral sleeve 140. Accordingly, the device 10, 10' according to the present invention may be safely and securely stored with minimal risk of evaporation, weight loss, and accidental operation.

The foregoing description discloses only non-limiting embodiments of the present invention. Modification of the above-disclosed exemplary click pen applicator device, and a method of using the same, which fall within the scope of the invention, will be readily apparent to those of ordinary skill in the art.

Accordingly, while the present invention has been disclosed in connection with the above non-limiting embodiments, it should be understood that other embodiments may fall within the spirit and scope of the invention, as defined by the following claims.

What is claimed is:

1. A method of priming and dosing a formulation using a click pen dispensing device, the method comprising:
   priming the formulation at a priming rate using a click actuator with a piston seat having two sets of external threads on a shaft with an unthreaded length therebetween; and
   dosing the formulation at a dosing rate different from the priming rate using the click actuator.

2. The method according to claim 1, wherein the click actuator is actuated using one hand.

3. The method according to claim 1, wherein the click actuator includes a locking element for preventing the priming and the dosing.

4. The method according to claim 1, wherein the formulation comprises salicylic acid.

5. The method according to claim 1, wherein the priming step includes at least one fine priming rate and a gross priming rate.

6. The method according to claim 1, wherein the dosing step dispenses a predetermined dose of the formulation, and the priming step dispenses a predetermined priming dose of the formulation.

7. A method of dispensing a formulation, using a device comprising a centerband having a proximal end and a distal end and defining a storage section having the formulation disposed within, an applicator section situated at the distal end of the centerband, and a multistage actuator section situated at the proximal end of the centerband, the method comprising:
   priming the device by priming actuations of the multistage actuator section with a piston seat having two sets of external threads on a shaft with an unthreaded length therebetween, the priming step comprising a gross priming actuation displacing a volume greater than that of a predetermined dose;
   dispensing the predetermined dose of the formulation, via the applicator section, by subsequent dispensing actuations of the multistage actuator section; and
   applying the predetermined dose via the applicator section.

8. The method according to claim 7, wherein the priming step comprises at least one fine priming actuation displacing a volume less than that of the gross priming actuation.

9. The method according to claim 7, wherein the priming step comprises at least one fine priming actuation displacing a volume equal to that of the predetermined dose.

* * * * *